United States Patent
Voegele et al.

(10) Patent No.: US 8,945,163 B2
(45) Date of Patent: Feb. 3, 2015

(54) METHODS AND DEVICES FOR CUTTING AND FASTENING TISSUE

(75) Inventors: James W. Voegele, Cincinnati, OH (US); William B. Weisenburgh, II, Maineville, OH (US); Christopher J. Hess, Cincinnati, OH (US); Michael A. Murray, Bellevue, KY (US); Robert P. Gill, Mason, OH (US); Darrel M. Powell, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1106 days.

(21) Appl. No.: 12/416,546

(22) Filed: Apr. 1, 2009

(65) Prior Publication Data

US 2010/0256634 A1 Oct. 7, 2010

(51) Int. Cl.
A61B 17/072 (2006.01)
A61B 17/125 (2006.01)
A61B 17/02 (2006.01)
A61B 17/00 (2006.01)
A61B 19/00 (2006.01)
(Continued)

(52) U.S. Cl.
CPC ....... *A61B 17/0218* (2013.01); *A61B 17/00234* (2013.01); *A61B 17/07207* (2013.01); *A61B 19/26* (2013.01); *A61B 2017/00278* (2013.01); *A61B 2017/00818* (2013.01); *A61B 2017/07285* (2013.01); *A61B 2017/320052* (2013.01); *A61B 2017/3466* (2013.01)
USPC .......................... 606/170; 227/180.1; 606/142

(58) Field of Classification Search
USPC ............ 227/175.1, 180.1; 606/139, 167, 170, 606/219, 205–209
See application file for complete search history.

(56) References Cited

U.S. PATENT DOCUMENTS 2,129,391 A 9/1938 Wappler
3,402,710 A 9/1968 Paleschuck
(Continued)

FOREIGN PATENT DOCUMENTS

EP 0568383 11/1993
EP 0646358 4/1995
(Continued)

OTHER PUBLICATIONS

Extended European Search Report for EP10250704.3 dated Dec. 3, 2010 (7 pages).

(Continued)

*Primary Examiner* — Ryan Severson
*Assistant Examiner* — Rachel S Papeika
(74) *Attorney, Agent, or Firm* — Mintz Levin Cohn Ferris Glovsky and Popeo, P.C.

(57) ABSTRACT

Methods and devices are provided for cutting and fastening tissue. In one embodiment, a surgical device can be used to at least partially transect a stomach by not cutting and/or not fastening a portion of tissue engaged in an end effector located at the device's distal end. A portion of the stomach can be engaged by the end effector, and the end effector can be actuated to cut and/or to apply one or more fasteners to tissue engaged in a distal portion of the end effector but not to cut and/or apply fasteners to tissue engaged in a proximal portion of the end effector. In a similar way, the surgical device can be used in any surgical procedure in which it is desired to cut and/or fasten a distal portion of tissue engaged by the end effector but not a proximal portion of tissue engaged by the end effector.

17 Claims, 24 Drawing Sheets

(51) Int. Cl.
*A61B 17/32* (2006.01)
*A61B 17/34* (2006.01)

(56) References Cited

U.S. PATENT DOCUMENTS

| | | | |
|---|---|---|---|
| 3,654,965 A | 4/1972 | Gramain | |
| 4,112,932 A | 9/1978 | Chiulli | |
| 4,306,545 A | 12/1981 | Ivan et al. | |
| 4,402,683 A | 9/1983 | Kopman | |
| 4,417,888 A | 11/1983 | Cosentino et al. | |
| 5,180,092 A * | 1/1993 | Crainich | 227/180.1 |
| 5,183,464 A | 2/1993 | Dubrul et al. | |
| 5,183,471 A | 2/1993 | Wilk | |
| 5,197,955 A | 3/1993 | Stephens et al. | |
| 5,207,213 A | 5/1993 | Auhll et al. | |
| 5,209,737 A | 5/1993 | Ritchart et al. | |
| 5,209,741 A | 5/1993 | Spaeth | |
| 5,269,772 A | 12/1993 | Wilk | |
| 5,285,945 A | 2/1994 | Brinkerhoff et al. | |
| 5,308,336 A | 5/1994 | Hart et al. | |
| 5,320,611 A | 6/1994 | Bonutti et al. | |
| 5,366,478 A | 11/1994 | Brinkerhoff et al. | |
| 5,385,553 A | 1/1995 | Hart et al. | |
| 5,385,560 A | 1/1995 | Wulf | |
| 5,391,154 A | 2/1995 | Young | |
| 5,395,367 A | 3/1995 | Wilk | |
| 5,431,676 A | 7/1995 | Dubrul et al. | |
| 5,443,452 A | 8/1995 | Hart et al. | |
| 5,443,484 A | 8/1995 | Kirsch et al. | |
| 5,480,410 A | 1/1996 | Cuschieri et al. | |
| 5,485,947 A * | 1/1996 | Olson et al. | 227/176.1 |
| 5,492,304 A | 2/1996 | Smith et al. | |
| 5,535,935 A * | 7/1996 | Vidal et al. | 227/175.2 |
| 5,545,179 A | 8/1996 | Williamson, IV | |
| 5,569,205 A | 10/1996 | Hart et al. | |
| 5,569,254 A | 10/1996 | Carlson et al. | |
| 5,634,911 A | 6/1997 | Hermann et al. | |
| 5,634,937 A | 6/1997 | Mollenauer et al. | |
| 5,643,301 A | 7/1997 | Mollenauer | |
| 5,653,705 A | 8/1997 | de la Torre et al. | |
| 5,672,168 A | 9/1997 | de la Torre et al. | |
| 5,676,657 A | 10/1997 | Yoon | |
| 5,695,448 A | 12/1997 | Kimura et al. | |
| 5,752,970 A | 5/1998 | Yoon | |
| 5,814,058 A | 9/1998 | Carlson et al. | |
| 5,826,776 A * | 10/1998 | Schulze et al. | 227/176.1 |
| 5,827,319 A | 10/1998 | Carlson et al. | |
| 5,865,807 A | 2/1999 | Blake, III | |
| 5,891,013 A | 4/1999 | Thompson | |
| 5,906,577 A | 5/1999 | Beane et al. | |
| 5,957,913 A | 9/1999 | de la Torre et al. | |
| 5,990,382 A | 11/1999 | Fox | |
| 5,997,515 A | 12/1999 | de la Torre et al. | |
| 6,004,303 A | 12/1999 | Peterson | |
| 6,024,736 A | 2/2000 | de la Torre et al. | |
| 6,066,090 A | 5/2000 | Yoon | |
| 6,077,288 A | 6/2000 | Shimomura et al. | |
| 6,086,603 A | 7/2000 | Termin et al. | |
| 6,120,513 A | 9/2000 | Bailey et al. | |
| 6,123,689 A | 9/2000 | To et al. | |
| 6,131,789 A * | 10/2000 | Schulze et al. | 227/175.4 |
| 6,162,196 A | 12/2000 | Hart et al. | |
| 6,217,555 B1 | 4/2001 | Hart et al. | |
| 6,245,052 B1 | 6/2001 | Orth et al. | |
| 6,258,069 B1 | 7/2001 | Carpentier et al. | |
| 6,277,064 B1 | 8/2001 | Yoon | |
| 6,315,770 B1 | 11/2001 | de la Torre et al. | |
| 6,319,246 B1 | 11/2001 | de la Torre et al. | |
| 6,328,730 B1 | 12/2001 | Harkrider, Jr. | |
| 6,348,034 B1 | 2/2002 | Thompson | |
| 6,352,503 B1 | 3/2002 | Matsui et al. | |
| 6,440,061 B1 | 8/2002 | Wenner et al. | |
| 6,447,489 B1 | 9/2002 | Peterson | |
| 6,454,783 B1 | 9/2002 | Piskun | |
| 6,458,077 B1 | 10/2002 | Boebel et al. | |
| 6,551,270 B1 | 4/2003 | Bimbo et al. | |
| 6,551,282 B1 | 4/2003 | Exline et al. | |
| 6,589,167 B1 | 7/2003 | Shimomura et al. | |
| 6,605,063 B2 | 8/2003 | Bousquet | |
| 6,613,038 B2 | 9/2003 | Bonutti et al. | |
| 6,669,674 B1 | 12/2003 | Macoviak et al. | |
| 6,702,787 B2 | 3/2004 | Racenet et al. | |
| 6,706,033 B1 | 3/2004 | Martinez et al. | |
| 6,706,050 B1 | 3/2004 | Giannadakis | |
| 6,786,382 B1 | 9/2004 | Hoffman | |
| 6,807,965 B1 | 10/2004 | Hickle | |
| 6,905,057 B2 | 6/2005 | Swayze et al. | |
| 6,908,430 B2 | 6/2005 | Caldwell et al. | |
| 6,939,296 B2 | 9/2005 | Ewers et al. | |
| 6,945,932 B1 | 9/2005 | Caldwell et al. | |
| 6,959,852 B2 | 11/2005 | Shelton, IV et al. | |
| 6,964,363 B2 | 11/2005 | Wales et al. | |
| 6,972,026 B1 | 12/2005 | Caldwell et al. | |
| 6,981,628 B2 | 1/2006 | Wales | |
| 7,000,819 B2 | 2/2006 | Swayze et al. | |
| 7,014,628 B2 | 3/2006 | Bousquet | |
| 7,052,454 B2 | 5/2006 | Taylor | |
| 7,055,731 B2 | 6/2006 | Shelton, IV et al. | |
| 7,111,769 B2 | 9/2006 | Wales et al. | |
| 7,118,528 B1 | 10/2006 | Piskun | |
| 7,163,510 B2 | 1/2007 | Kahle et al. | |
| 7,201,734 B2 | 4/2007 | Hickle | |
| 7,214,185 B1 | 5/2007 | Rosney et al. | |
| 7,247,154 B2 | 7/2007 | Hickle | |
| 7,338,473 B2 | 3/2008 | Campbell et al. | |
| 7,344,547 B2 | 3/2008 | Piskun | |
| 7,364,061 B2 | 4/2008 | Swayze et al. | |
| 7,393,322 B2 | 7/2008 | Wenchell | |
| 7,413,559 B2 | 8/2008 | Stubbs et al. | |
| 7,434,715 B2 | 10/2008 | Shelton, IV et al. | |
| 7,588,177 B2 * | 9/2009 | Racenet | 227/181.1 |
| 7,918,230 B2 * | 4/2011 | Whitman et al. | 128/898 |
| 2002/0156432 A1 | 10/2002 | Racenet et al. | |
| 2003/0028179 A1 | 2/2003 | Piskun | |
| 2003/0139756 A1 | 7/2003 | Brustad | |
| 2004/0015185 A1 | 1/2004 | Ewers et al. | |
| 2004/0106942 A1 | 6/2004 | Taylor et al. | |
| 2004/0138528 A1 | 7/2004 | Richter et al. | |
| 2004/0199181 A1 * | 10/2004 | Knodel et al. | 606/139 |
| 2004/0215063 A1 | 10/2004 | Bonadio et al. | |
| 2004/0230160 A1 | 11/2004 | Blanco | |
| 2004/0254426 A1 | 12/2004 | Wenchell | |
| 2005/0020884 A1 | 1/2005 | Hart et al. | |
| 2005/0033342 A1 | 2/2005 | Hart et al. | |
| 2005/0085842 A1 | 4/2005 | Eversull et al. | |
| 2005/0137609 A1 | 6/2005 | Guiraudon | |
| 2005/0148823 A1 | 7/2005 | Vaugh et al. | |
| 2005/0155611 A1 | 7/2005 | Vaugh et al. | |
| 2005/0192483 A1 | 9/2005 | Bonadio et al. | |
| 2005/0209608 A1 | 9/2005 | O'Heeron | |
| 2005/0222582 A1 | 10/2005 | Wenchell | |
| 2005/0267419 A1 | 12/2005 | Smith | |
| 2005/0273132 A1 | 12/2005 | Shluzas et al. | |
| 2005/0277946 A1 | 12/2005 | Greenhalgh | |
| 2006/0019592 A1 | 1/2006 | Kupferberg et al. | |
| 2006/0019723 A1 | 1/2006 | Vorenkamp et al. | |
| 2006/0020241 A1 | 1/2006 | Piskun et al. | |
| 2006/0020281 A1 | 1/2006 | Smith | |
| 2006/0024500 A1 | 2/2006 | Seo | |
| 2006/0042636 A1 | 3/2006 | Nalagatla et al. | |
| 2006/0071432 A1 | 4/2006 | Staudner | |
| 2006/0212062 A1 | 9/2006 | Farascioni | |
| 2006/0224129 A1 | 10/2006 | Beasley et al. | |
| 2006/0224164 A1 | 10/2006 | Hart et al. | |
| 2006/0229501 A1 | 10/2006 | Jensen et al. | |
| 2006/0241651 A1 | 10/2006 | Wilk | |
| 2006/0241671 A1 | 10/2006 | Greenhalgh | |
| 2006/0247500 A1 | 11/2006 | Voegele et al. | |
| 2006/0247673 A1 | 11/2006 | Voegele et al. | |
| 2006/0264706 A1 | 11/2006 | Piskun | |
| 2006/0271075 A1 | 11/2006 | Bilotti et al. | |
| 2007/0049966 A1 | 3/2007 | Bonadio et al. | |
| 2007/0060939 A1 | 3/2007 | Lancial et al. | |
| 2007/0085232 A1 | 4/2007 | Brustad et al. | |

(56) References Cited

U.S. PATENT DOCUMENTS

| | | |
|---|---|---|
| 2007/0088202 A1 | 4/2007 | Albrecht et al. |
| 2007/0088277 A1 | 4/2007 | McGinley et al. |
| 2007/0118021 A1 | 5/2007 | Pokorney |
| 2007/0151566 A1 | 7/2007 | Kahle et al. |
| 2007/0175961 A1 | 8/2007 | Shelton et al. |
| 2007/0208312 A1 | 9/2007 | Norton et al. |
| 2007/0255219 A1 | 11/2007 | Vaugh et al. |
| 2007/0260121 A1 | 11/2007 | Bakos et al. |
| 2007/0260273 A1 | 11/2007 | Cropper et al. |
| 2008/0027476 A1 | 1/2008 | Piskun |
| 2008/0051739 A1 | 2/2008 | McFarlane |
| 2008/0065021 A1 | 3/2008 | Jenkins et al. |
| 2008/0078808 A1 | 4/2008 | Hess et al. |
| 2008/0119821 A1 | 5/2008 | Agnihotri et al. |
| 2008/0255519 A1 | 10/2008 | Piskun et al. |
| 2009/0126744 A1 | 5/2009 | Bessler et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |

FOREIGN PATENT DOCUMENTS

| | | | | |
|---|---|---|---|---|
| EP | 950376 | | 10/1999 | |
| EP | 1350476 | | 10/2003 | |
| EP | 1731105 A1 | | 12/2006 | |
| EP | 1927319 A2 | | 6/2008 | |
| FR | 2710270 | | 3/1995 | |
| JP | 2006320750 | | 11/2006 | |
| WO | WO-2005087112 | | 9/2005 | |
| WO | WO-2005094432 | | 10/2005 | |
| WO | WO-2006019592 | | 2/2006 | |
| WO | WO-2006019723 | | 2/2006 | |
| WO | WO-2006035446 | | 4/2006 | |
| WO | WO-2007119232 | | 10/2007 | |
| WO | WO-2008024502 | | 2/2008 | |
| WO | WO-2008093313 | | 8/2008 | |
| WO | WO-2008149332 | | 12/2008 | |
| WO | WO2009/039510 | * | 3/2009 | ............. A61B 17/10 |
| WO | WO-2009039510 A1 | | 3/2009 | |

OTHER PUBLICATIONS

Ahmad G, Duffy JM, Phillips K, Watson A., "Laparoscopic Entry Techniques" Cochrane Database Syst Rev., (2):CD006583, Apr. 16, 2008.

Bucher P, Pugin F, Morel P., "Single Port Access Laparoscopic Right Hemicolectomy" Int J Colorectal Dis., Jul. 8, 2008.

Canes D, Desai MM, Aron M, Haber GP, Goel RK, Stein RJ, Kaouk JH, Gill IS., "Transumbilical Single-Port Surgery: Evolution and Current Status" Eur Urol., Jul. 14, 2008.

Gill IS, Canes D, Aron M, Haber GP, Goldfarb DA, Flechner S, Desai MR, Kaouk JH, Desai MM., "Single Port Transumbilical (E-Notes) Donor Nephrectomy" Journal Urol., 180(2):637-41; Aug. 2008.

Goel RK, Kaouk JH., "Single Port Access Renal Cryoablation (SPARC): A New Approach" Eur Urol. Jun. 2008;53(6):1204-9. Epub Mar. 18, 2008.

Johnston D, Dachtler J, Sue-Ling HM, King RF, Martin I. G, Roderick F.G. "The Magenstrasse and Mill Operation for Morbid Obesity" Obesity Surgery, Apr. 2003.

K. Sumiyama, C. Gostout, E.Rajan, T.Bakken, M.Knipschield, S.Chung, P.Cotton, R.Hawes, A.Kalloo, A.Kalloo, S.Kantsevoy and P.Pasricha "Transgastric Cholecystectomy: Transgastric Accessibility to The Gallbladder Improved with the SEMF Method and a Novel Multibending Therapeutic Endoscope" Gastrointestinal Endoscopy, vol. 65, Issue 7, Jun. 2007.

Kaouk JH, Haber GP, Goel RK, Desai MM, Aron M, Rackley RR, Moore C, Gill IS., "Single-port Laparoscopic Surgery in Urology: Iniitial Experience", Urology., 71(1):3-6., Jan. 2008.

Kaouk JH, Palmer JS., "Single-port Laparoscopic Surgery: Initial Experience in Children for Varicocelectomy" BJU Int.;102(1):97-9. Epub Mar. 5, 2008.

Ponsky LE, Cherullo EE, Sawyer M, Hartke D., "Single Access Site Laparoscopic Radical Nephrectomy: Initial Clinical Experience" J Endourol., 22(4):663-6, Apr. 2008.

Ponsky TA, Lukish JR., "Single Site Laparoscopic Gastrostomy with a 4-mm Bronchoscopic Optical Grasper" J Pediatric Surgery, 43(2):412-4, Feb. 2008.

Product Brochure "Access the Future of Laparoscopic Surgery" Advanced Surgical Concepts Limited, Inc.

Rane A, Rao P, Rao P. Single-port-access Nephrectomy and Other Laparoscopic Urologic Procedures Using a Novel Laparoscopic Port (R-port), Urology. (2):260-3; discussion, Epub May 12, 2008.

Vassallo C, et al. "The Super-Magenstrasse and Mill Operation with Pyloroplasty: Preliminary Results", Obesity Surgery, 17, Aug. 2007.

Web Page www.websurg.com/notes/videos.php <http://www.websurg.com/notes/videos.php>, Screenshots videos "Notes Hybrid Sleeve Gastrectomy Performed During Course" Vix, MD; Solano, MD; Asakuma, MD, Feb. 2008.

Web Page www.websurg.com/notes/videos.php <http://www.websurg.com/notes/videos.php>, Screenshots videos "Transvaginal Hybrid Notes Sleeve Gastrectomy Porcine Model" Vix, MD; Solano, MD; Asakuma, MD, Dec. 2007.

\* cited by examiner

FIG. 9
FIG. 10
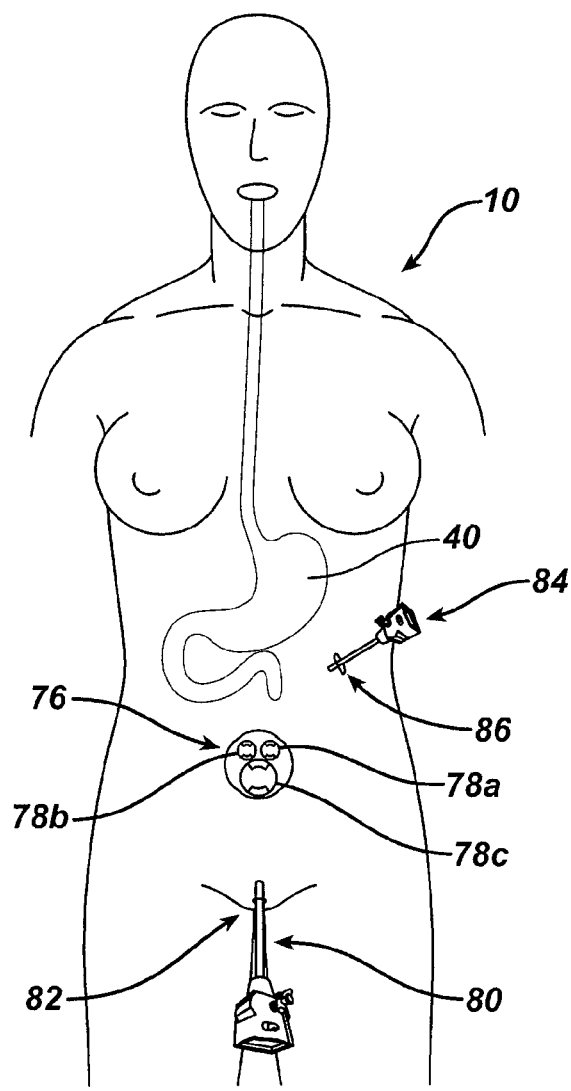
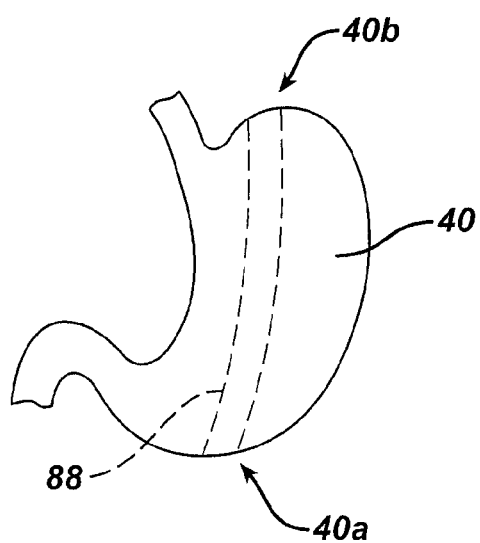

METHODS AND DEVICES FOR CUTTING AND FASTENING TISSUE

FIELD OF THE INVENTION

The present invention relates to methods and devices for cutting and fastening tissue, and in particular to methods and devices for performing gastroplasties.

BACKGROUND OF THE INVENTION

Obesity is becoming a growing concern, particularly in the United States, as the number of obese people continues to increase and more is learned about the negative health effects of obesity. Morbid obesity, in which a person is 100 pounds or more over ideal body weight, in particular poses significant risks for severe health problems. Accordingly, a great deal of attention is being focused on treating obese patients. Surgical procedures to treat morbid obesity have included gastric bypasses (stomach stapling), adjustable gastric banding, and vertical banded gastroplasty and sleeve gastrectomies (removal of all or a portion of the stomach). Such surgical procedures have increasingly been performed laparoscopically. Reduced post-operative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, multiple abdominal incisions are often required in such obesity treatment procedures, thereby increasing chances for undesirable post-operative consequences such as cosmetic scarring.

Gastroplasties have become increasingly favored by surgeons and patients for treating obesity, as well as for treating stomach diseases such as cancer where a portion of the stomach is removed, because gastroplasties do not leave any foreign material in a patient and do not require a complicated intestinal bypass. Instead, the stomach's volume is reduced through partial division of the stomach, thereby leaving a stomach "sleeve" between the esophagus and intestine. A laparoscopic gastroplasty procedure generally involves insufflation of the abdominal cavity with carbon dioxide gas to a pressure of around 15 millimeters of mercury (mm Hg). The abdominal wall is pierced and a 5-10 mm in diameter straight tubular cannula or trocar is inserted into the abdominal cavity. A laparoscopic telescope connected to an operating room monitor is used to visualize the operative field and is placed through one of the trocar(s). Laparoscopic instruments are placed through two or more additional trocars for manipulation by the surgeon and surgical assistant(s). Thus, such laparoscopic procedures can require multiple instruments to be introduced into a patient through multiple, potentially scarring incisions and/or can result in interference between instruments near each other. The placement of two or more standard cannulas and laparoscopic instruments in the abdomen next to each other and/or placement of two or more instruments into the abdomen through the same incision creates a so-called "chopstick" effect, which describes interference between the surgeon's hands, between the surgeon's hands and the instruments, and between the instruments. This interference greatly reduces the surgeon's ability to perform a described procedure. Further, in a Magenstrasse and Mill gastroplasty procedure in which only a portion of the stomach is cut to form the stomach sleeve, a starting location for the stomach sleeve must be identified, which can require additional instrumentation and surgical time.

Accordingly, there remains a need for methods and devices for cutting and fastening tissue that minimize patient recovery time, improve cosmetic outcome, reduce the "chopstick" effect, and minimize surgical procedure duration.

SUMMARY OF THE INVENTION

The present invention generally provides methods and devices for cutting and fastening tissue. In one embodiment, a surgical device is provided that includes first and second jaws that can be movable relative to one another and that can engage tissue therebetween. The device also includes a cutting element that can translate between a proximal end to a distal end of the first and second jaws. The cutting element can be movable between a first position in a proximal region of the first and second jaws in which tissue is not cut and a second position in a distal region of the first and second jaws in which tissue is cut.

The device can have any number of variations. For example, the cutting element can pivot between the first and second positions as the cutting element translates through the first and second jaws. The cutting element can include a cut-out formed therein that can allow the cutting element to pivot between the first and second positions. For another example, at least one of the first and second jaws can include a cam element that can move the cutting element from one of the first and second positions to another of the first and second positions as the cutting element translates through the first and second jaws. For still another example, the cutting element can translate in a distal to proximal direction through the first and second jaws to cut tissue, and/or the cutting element can translate in a distal to proximal direction through the first and second jaws to cut tissue. For yet another example, the proximal region can comprise at least 50% of a total length extending between the proximal and distal ends of the first and second jaws.

In another embodiment, a surgical device is provided that includes an elongate shaft, and an end effector that is coupled to a distal end of the elongate shaft and that can engage tissue. The device also includes a cutting element that can translate between a proximal end to a distal end of the end effector. The cutting element can be movable between a first position in a proximal region of the end effector in which tissue is not cut and a second position in a distal region of the end effector in which tissue is cut.

The device can vary in any number of ways. For example, the cutting element can translate in a distal to proximal direction along the end effector to cut tissue. As another example, the cutting element can rotate between the first and second positions. As yet another example, the device can include a cam element that can move the cutting element from one of the first and second positions to another of the first and second positions during translation of the cutting element along the end effector. As still another example, the proximal region can comprise at least 50% of a total length extending between the proximal and distal ends of the end effector.

In another aspect, a surgical method is provided that includes advancing a surgical device into a body cavity of a patient, engaging a portion of a stomach of the patient between first and second jaws of an end effector at a distal end of the surgical device, and translating a cutting element along proximal and distal regions of the first and second jaws such that tissue engaged in the proximal region is not cut by the cutting element and such that tissue engaged in the distal region is cut by the cutting element.

The method can have any number of variations. For example, during translation of the cutting element along the first and second jaws, the method can include moving the cutting element relative to the first and second jaws between a first position in the proximal region of the first and second jaws and a second position in the distal region of the first and second jaws for another example, translating a cutting element along proximal and distal regions of the first and second jaws can include moving the cutting element in a proximal to distal direction along the first and second jaws. For yet another example, prior to engaging a portion of the stomach between first and second jaws of the end effector, the method can include positioning a proximal end of the end effector substantially at an antrum of the stomach and positioning a distal end of the end effector a distance proximal to an angle of His of the stomach. For still another example, translating a cutting element along proximal and distal regions of the first and second jaws can include cutting the stomach from a location proximal to an antrum of the stomach and through an angle of His of the stomach. For another example, translating a cutting element along proximal and distal regions of the first and second jaws can include forming a first slit formed in an anterior wall of the stomach and a second, separate slit formed in a posterior wall of the stomach. For yet another example, advancing a surgical device into a body cavity of a patient can include advancing the surgical device through one of an abdominal access hole formed in the patient or a vaginal access hole formed in the patient.

In another embodiment, a surgical device is provided that includes first and second jaws movable relative to one another and having a distal region that is configured to cut and to deliver a plurality of fasteners to tissue engaged in the distal region of the first and second jaws, and a proximal region that is configured to engage tissue without fastening and without cutting the tissue.

The device can have any number of variations. For example, the device can include a plurality of fasteners disposed in the distal region of the first and second jaws. The device can also include a cartridge disposed in one of the first and second jaws and having a distal region that contains the plurality of fasteners therein, and a proximal region that is free of the fasteners. In one embodiment, the proximal region can comprise at least about 20% of a total length extending between proximal and distal ends of the first and second jaws. The device can also include a cutting element that can continuously translate through the proximal and distal regions and cut tissue engaged in the distal region and not cut tissue engaged in the proximal region. The cutting element can be movable between a first position in the proximal region and a second position rotated from the first position in the distal region, where the cutting element in the first position cannot cut tissue engaged by the first and second jaws and in the second position can cut tissue engaged by the first and second jaws. In some embodiments, at least one of the first and second jaws can include a cam element that can move the cutting element from one of the first and second positions to another of the first and second positions during translation of the cutting element through the first and second jaws.

In another embodiment, a surgical device is provided that includes an elongate shaft and an end effector coupled to a distal end of the elongate shaft. The end effector can have a distal region that can deliver a plurality of fasteners to tissue engaged therein, and a proximal fastener-free region that can engage tissue. The device can also include a cutting element that can translate along the end effector to cut tissue engaged by the distal region without cutting tissue engaged by the proximal fastener-free region of the end effector.

In one embodiment, the cutting element can be movable between a first position in the proximal region in which tissue is not cut and a second position in the distal region in which tissue is cut. The device can also include a cam element that can move the cutting element from one of the first and second positions to another of the first and second positions during translation of the cutting element along the end effector. The cutting element can rotate between the first and second positions during translation of the cutting element along the end effector. The cutting element can also translate in a proximal to distal direction or in a distal to proximal direction along the end effector to cut tissue. In another embodiment, a longitudinal length of the proximal region can be greater than a longitudinal length of the distal region.

In another aspect, a surgical method is provided that includes advancing a surgical device into a body cavity of a patient, engaging anterior and posterior walls of a stomach of the patient with an end effector on a distal end of the surgical device such that a folded edge of the stomach is positioned in a proximal region of the end effector, and actuating the surgical device to form a transection in the stomach without transecting the folded edge of the stomach.

The method can have any number of variations. For example, actuating the surgical device can include moving a cutting element through the proximal region of the end effector without cutting the folded edge and the anterior and posterior walls of the stomach engaged by the proximal region of the end effector, and moving the cutting element through a distal region of the end effector to cut the anterior and posterior walls of the stomach engaged by the distal region of the end effector. As another example, actuating the surgical device can include delivering a plurality of fasteners to the anterior and posterior walls of the stomach engaged by a distal region of the end effector without delivering any fasteners to the folded edge and the anterior and posterior walls of the stomach engaged by the proximal region of the end effector. As yet another example, forming a transection in the stomach without transecting the folded edge of the stomach can include transecting the stomach from a location proximal to an antrum of the stomach and through an angle of His of the stomach. As still another example, forming a transection in the stomach without transecting the folded edge of the stomach can include forming a first slit formed in the anterior wall and a second, separate slit formed in the posterior wall. As another example, advancing a surgical device into a body cavity of a patient can include advancing the surgical device through one of an abdominal access hole formed in the patient or a vaginal access hole formed in the patient.

BRIEF DESCRIPTION OF THE DRAWINGS

The invention will be more fully understood from the following detailed description taken in conjunction with the accompanying drawings, in which:

FIG. 9 is a perspective partially transparent view of one embodiment of a patient having an access hole formed in a vaginal wall of the patient, a first abdominal port formed at an umbilicus of the patient, and a second abdominal port formed in an abdominal wall of the patient;

FIG. 10 is a perspective view of one embodiment of a tunnel formed underneath a stomach of a patient;

DETAILED DESCRIPTION OF THE INVENTION

Figure 1:
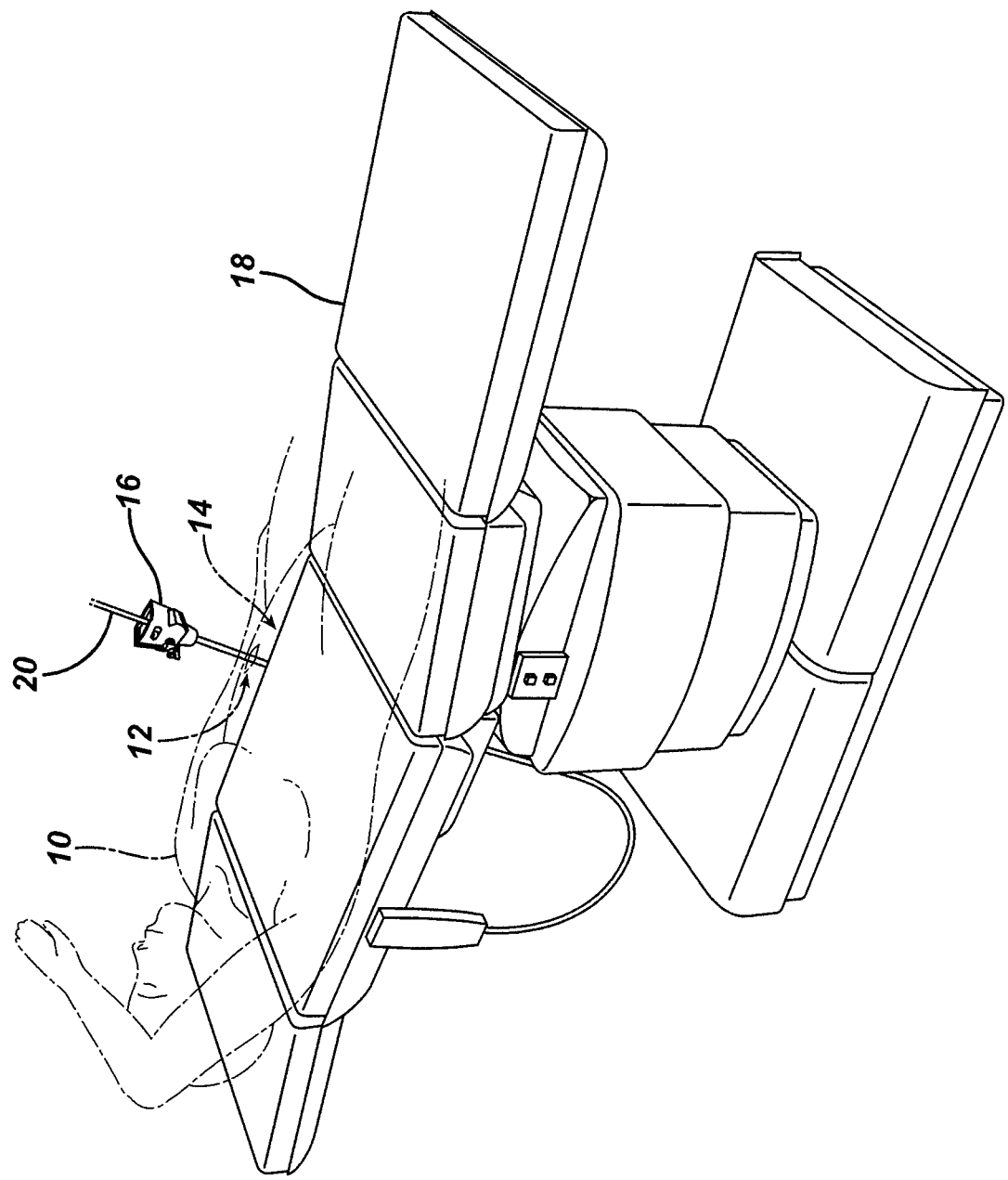
FIG. 1 is a perspective partially transparent view of one embodiment of a patient having an access hole formed in an abdominal wall of the patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for cutting and fastening tissue. A person skilled in the art will appreciate that while the methods and devices are described in connection with a gastroplasty, the methods and devices disclosed herein can be used in numerous surgical procedures. By way of non-limiting example, the devices can be used in laparoscopic procedures, in which the devices are introduced percutaneously. The methods and devices can also be used in open surgical procedures. Furthermore, the surgical devices can be configured to pass through any portion of a body, but in an exemplary embodiment, the surgical devices are configured to pass through an abdominal access hole or a vaginal access hole.

In one embodiment, a method of performing a gastroplasty includes gaining access to a stomach of a patient through one or more openings formed in one or more of the patient's digestive tract, abdominal wall, and vaginal wall. In an exemplary embodiment, the methods and devices are used to perform a Magenstrasse and Mill procedure in which only a portion of the stomach is transected. Various instruments can be inserted through various access holes in the patient to perform certain steps, such as tensioning and cutting tissue, sizing and transecting the stomach, viewing the surgical site, etc. In an exemplary embodiment, a surgical device is provided that can be used to at least partially transect the stomach. The device can have an end effector that can engage tissue, and that can be actuated to cut and/or to apply one or more fasteners to tissue engaged in a distal portion of the end effector without cutting and/or applying fasteners to tissue engaged in a proximal portion of the end effector. In this way, in a Magenstrasse and Mill procedure where the stomach is not fully transected between the stomach's angle of His and the stomach's pylorus, a device that does not cut and/or fasten tissue engaged in a proximal region of an end effector can be used to engage the stomach's antrum without cutting the antrum and instead can cut and fasten tissue apart from the antrum, i.e., tissue engaged in the distal portion of the device. Use of the device can reduce the need to measure, calculate, mark, etc., the stomach 40 to determine a starting location for the stomach transection because the device can generally predetermine the transection's starting location by a proximal cut-free and/or fastener-free region with a predetermined length. In a similar way, the surgical device can be used in any surgical procedure in which it is desired to cut and/or fasten a distal portion of tissue engaged by the end effector but not a proximal portion of tissue engaged by the end effector.

A patient can be prepared for a gastroplasty surgical procedure in any way, as will be appreciated by a person skilled in the art. For example, the patient can be fully sedated or consciously sedated for the procedure. Non-limiting embodiments of a conscious sedation system can be found in U.S. Patent Publication No. 2006/0042636 filed on Jun. 21, 2005 and entitled "Oral Nasal Cannula," U.S. Pat. No. 6,807,965 issued Oct. 26, 2004 and entitled "Apparatus And Method For Providing A Conscious Patient Relief From Pain And Anxiety Associated With Medical Or Surgical Procedures," U.S. Pat. No. 7,201,734 issued Apr. 10, 2007 and entitled "Apparatus For Drug Delivery In Association With Medical Or Surgical Procedures," U.S. Pat. No. 7,247,154 issued Jul. 24, 2007 and entitled "Method For Drug Delivery In Association With Medical Or Surgical Procedures," which are hereby incorporated by reference in their entireties.

In one exemplary embodiment of a gastroplasty procedure illustrated in FIG. 1, an abdominal opening or access hole 12 is formed in an abdominal wall 14 of a patient 10. During the gastroplasty, the patient 10 is preferably positioned as shown in a reclined, substantially horizontal lithotomy position on an examination table 18 to provide clear access to the patient's abdominal region. FIG. 1 and other figures discussed herein are simplified for ease of presentation and do not always illustrate the patient 10 and/or devices present at a given moment in a surgical procedure, such as devices shown in one or more previously described figures and any additional necessary equipment, e.g., patient monitoring equipment, safety devices, video monitors, etc. Furthermore, the gastroplasty is described as performed by a surgeon, but as will be appreciated by a person skilled in the art, one or more medical professionals, e.g., surgeons, surgical assistants, nurses, etc., can perform any one or more portions of the procedure. Also, while a female patient is illustrated, the patient 10 be male or female.

As shown in FIG. 1, the abdominal opening or access hole 12 can be formed in the abdominal wall 14, although an access hole can be used and/or be formed anywhere in the patient 10. The abdominal access hole 12 can be in the form of a substantially circular otomy, or it can be a percutaneous incision. A person skilled in the art will appreciate that the term "otomy" as used herein is intended to encompass an opening or access hole that is configured to accommodate an access device with a retractor or other device positionable in the access hole having an outer diameter in the range of about 15 to 35 mm, e.g., about 25.4 mm (about 1 inch). A person skilled in the art will also appreciate that the term "percutaneous opening" or "percutaneous access hole" as used herein is intended to encompass a relatively small opening or access hole in a patient that preferably has a diameter in a range of about 3 to 5 mm.

The abdominal access hole 12 can be formed in any way, as will be appreciated by a person skilled in the art. As illustrated, the abdominal access hole 12 is formed using a trocar 16. The trocar 16 can include any cannula configured to incise tissue and having a cannulated interior through which a surgical instrument can be passed into a patient through the incised tissue. The trocar 16 can include an optical tip configured to provide visualization of the abdominal wall 14 as the trocar 16 is passed therethrough, for example using a scoping device with a viewing element located thereon, e.g., a laparoscope 20, that is inserted into the trocar 16. The laparoscope 20 can be inserted into the trocar 16 at any time, including during penetration through tissue or after the trocar 16 penetrates the abdominal wall 14. A person skilled in the art will also appreciate that any one or more scoping devices used in the gastroplasty can each include any surgical device having a viewing element, e.g., a lens, located thereon. Non-limiting examples of a scoping device include an endoscope, a laparoscope, a gastroscope, and a colonoscope. The trocar 16 can be configured to allow a rigid or flexible surgical instrument, e.g., a grasper, a cutting instrument, a scoping device, etc., to be passed therethrough and into the patient's abdominal cavity. A person skilled in the art will appreciate that the term "grasper" as used herein is intended to encompass any surgical instrument that is configured to grab and/or attach to tissue and thereby manipulate the tissue, e.g., forceps, retractors, movable jaws, magnets, adhesives, stay sutures, etc.

In one embodiment, a scoping device inserted into the patient 10 can include one or more distal, flexible joints that can help orient the scoping device inside the patient 10. Non-limiting embodiments of flexible joints on a surgical device can be found in U.S. patent application Ser. No. 12/242,333 filed Sep. 30, 2008 and entitled "Methods And Devices For Performing Gastrectomies And Gastroplasties," U.S. patent application Ser. No. 12/242,353 filed Sep. 30, 2008 and entitled "Methods And Devices For Performing Gastrectomies And Gastroplasties," and U.S. patent application Ser. No. 12/242,381 filed Sep. 30, 2008 and entitled "Methods And Devices For Performing Gastroplasties Using A Multiple Port Access Device," which are hereby incorporated by reference in their entireties. In general, the flexible joint(s) can be configured to flex or bend. The flexible joint(s) can be passively actuated, e.g., moveable when abutted by one or more adjacent structures, and/or actively actuated, e.g., through manipulation of a mechanical and/or manual actuation mechanism. The flexible joint(s) can be configured to bend in a single direction when actuated, and the single direction can be selectively chosen, e.g., left, right, up, down, etc. If a surgical device includes a plurality of flexible joints, each of the flexible joints can be configured to be independently actuated in any direction same or different from any of the other flexible joints of the surgical device. The actuation mechanism can be configured to control the amount of movement in a chosen direction. The flexible joint(s) can be formed in any way, same or different from one another, as will be appreciated by a person skilled in the art. For non-limiting example, the flexible joint(s) can be made from a flexible material, can include one or more features formed therein to facilitate flexibility, e.g., a plurality of cut-outs, slots, etc., and/or can be formed from a plurality of linkages that are movably coupled to one another. In an alternate embodiment, a scoping device can have two or more flexible joints each at different locations along its longitudinal axis, with or without use of a sleeve, to allow the scoping device to bend in at least two directions relative to the scoping device's longitudinal axis. A non-limiting example of a multibending scoping device is the R-Scope XGIF-2TQ260ZMY available from Olympus Corp. of Tokyo, Japan.

Optionally, one or more openings or access holes in addition to the abdominal access hole 12 can be formed in the patient's abdominal wall 14. Each additional abdominal access hole can have any size, shape, and configuration, but in an exemplary embodiment, the additional abdominal access hole(s) are each percutaneous openings. Any of the additional abdominal access hole(s) can be formed before and/or after the abdominal access hole 12, but in an exemplary embodiment, any additional abdominal access hole(s) are formed after the abdominal access hole 12 to allow prior insufflation of the patient's abdominal cavity using a surgical device inserted through the abdominal access hole 12, as discussed further below.

Figure 2:
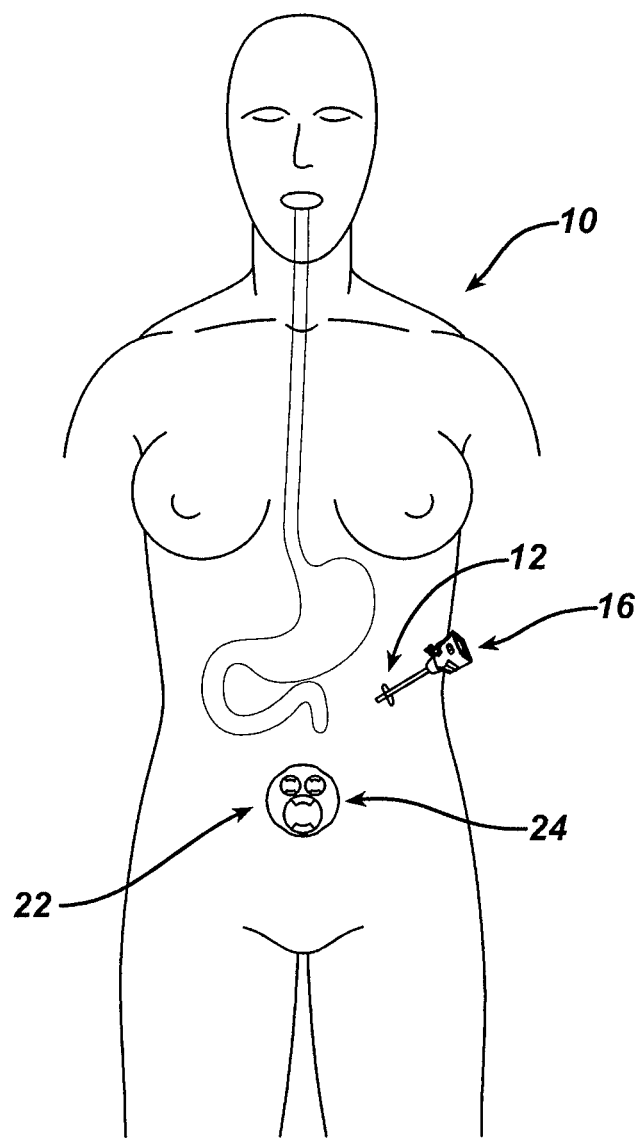
FIG. 2 is a perspective partially transparent view of the patient of FIG. 1 having a second access hole formed in the umbilicus of the patient.

FIG. 2 illustrates one embodiment of an additional abdominal opening or access hole 22 formed in the patient 10 in addition to the abdominal access hole 12 having the trocar 16 positioned therein. The additional abdominal opening 22 can have any size, shape, and configuration, but in an exemplary embodiment, the additional abdominal access hole 22 is an otomy an is located substantially at the patient' umbilicus. Smaller and fewer body cavity incisions can generally improve a patient's recovery time and reduce pain, so it can be advantageous to perform an operation utilizing only a single abdominal incision, such as one in the navel. The umbilicus is the thinnest and least vascularized, and a well-hidden, area of the abdominal wall 14. An umbilical incision can be easily enlarged, e.g., in order to eviscerate a larger specimen, without significantly compromising cosmesis and without increasing the chances of wound complications. The additional abdominal opening 22 can be formed in any way, as will be appreciated by a person skilled in the art. A multiple port access device 24 having two or more sealing ports through which surgical instruments can be inserted can be positioned in the abdominal wall 14 following creation of the additional abdominal access hole 22 in any way such as by using a cutting instrument, e.g., a needle knife, a scalpel, a hook knife, etc. The multiple port access device 24 can have any configuration, but non-limiting embodiments of a multiple port access device can be found in previously mentioned U.S. patent application Ser. No. 12/242,381 filed Sep. 30, 2008 and entitled "Methods And Devices For Performing Gastroplasties Using A Multiple Port Access Device" and in U.S. Patent Publication No. 2006/0247673 filed Apr. 5, 2006 and entitled "Multi-port Laparoscopic Access Device," U.S. patent application Ser. No. 12/242,765 filed Sep. 30, 2008 and entitled "Surgical Access Device," U.S. patent application Ser. No. 12/242,711 filed Sep. 30, 2008 and entitled "Surgical Access Device with Protective Element," U.S. patent application Ser. No. 12/242,721 filed Sep. 30, 2008 and entitled "Multiple Port Surgical Access Device," and U.S. patent application Ser. No. 12/242,726 filed Sep. 30, 2008 and entitled "Variable Surgical Access Device," which are hereby incorporated by reference in their entireties.

Figure 3:
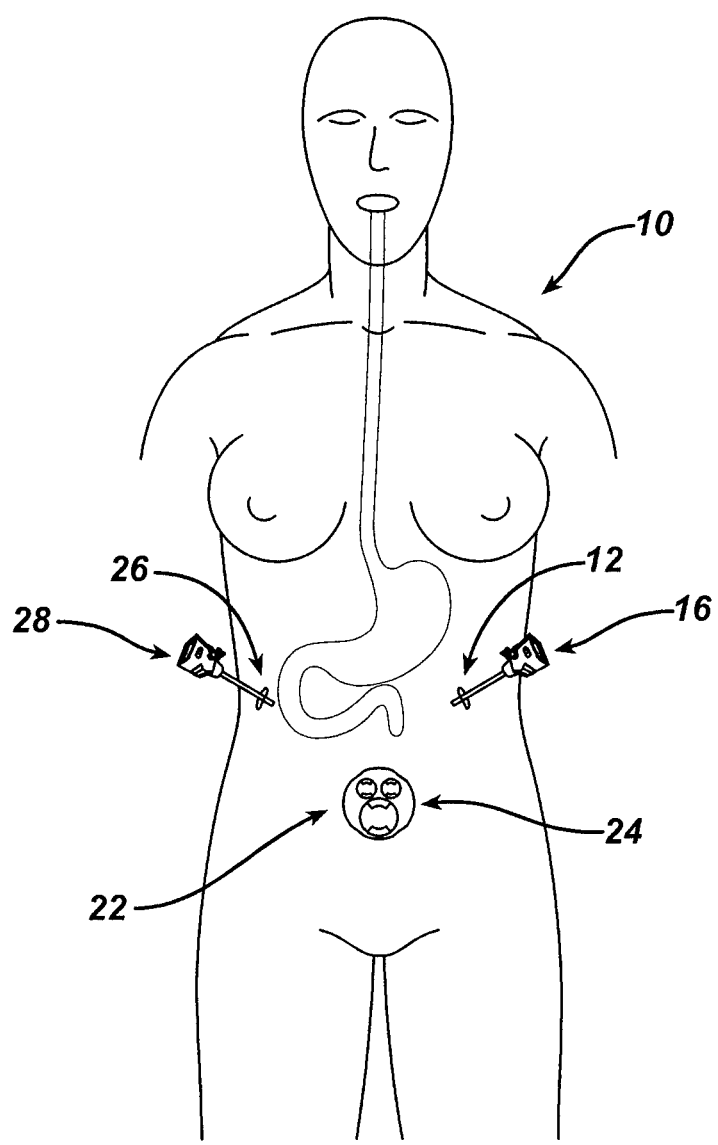
FIG. 3 is a perspective partially transparent view of the patient of FIG. 2 having a third access hole formed in the abdominal wall of the patient.

FIG. 3 shows another embodiment where, in addition to the abdominal access hole 12 and the additional abdominal access hole 22, a second additional abdominal opening or access hole 26 is formed in the patient's abdominal wall 14 to provide access to the patient's abdominal cavity. The second additional abdominal opening 26 can have any size, shape, and configuration, but in an exemplary embodiment, the second additional access hole 26 has a size, shape, and configuration substantially the same as the abdominal access hole 12. The additional abdominal access holes 22, 26 can be formed in any order with respect to one another and with respect to the abdominal opening 12 with the trocar 16 positioned therein. The abdominal access holes 12, 22, 26 can be positioned anywhere through the patient's abdominal wall 14, but as illustrated, the percutaneous abdominal access holes 12, 26 can be substantially laterally aligned on opposed sides of the patient's abdomen. The access hole 22 having the multiple port access device 24 positioned therein can, as illustrated, be non-laterally aligned with and be located between the percutaneous abdominal access holes 12, 26, e.g., in the umbilicus. In this way, a grasper can be inserted through at least one of the percutaneous abdominal access holes 12, 26 and can allow tissue to be tensioned in the patient 10 at a transverse angle relative to a surgical instrument, e.g., a cutting instrument, inserted into to the patient 10 through the umbilicus. As will be appreciated by a person skilled in the art, the second additional access hole 26 can be formed in any way through the patient's abdominal wall 14 to provide access to the patient's abdominal cavity, but in an exemplary embodiment it is formed using a trocar 28 in a way similar to that discussed above for the other percutaneous abdominal opening 12 created using the trocar 16. The trocars 16, 28 inserted through the percutaneous abdominal openings 12, 26 can include any trocar, same or different from each other.

As will be appreciated by a person skilled in the art, access holes in the patient 10 can be formed in any way. Non-limiting embodiments of a trocar that can be used to form an access hole can be found in U.S. Patent Publication No. 2007/0260273 filed May 8, 2006 and entitled "Endoscopic Translumenal Surgical Systems," which is hereby incorporated by reference in its entirety. An exemplary embodiment of a trocar can include a trocar housing configured to allow a surgical device to pass therethrough, and a trocar sleeve or overtube mated to or extending from the trocar housing. The trocar can also include an obturator configured to pass through the trocar housing and the trocar sleeve. The obturator can have an inner lumen formed therethrough for receiving a scoping device and/or other surgical device therein, and a distal end configured penetrate through tissue. The trocar sleeve can be slidably disposed over the obturator and can function as a placeholder after the trocar is inserted through tissue and the obturator is removed. Non-limiting embodiments of a sleeve and an obturator that can be used to form an abdominal access hole can be found in previously mentioned U.S. patent application Ser. No. 12/242,333 filed Sep. 30, 2008 and entitled "Methods And Devices For Performing Gastrectomies And Gastroplasties" and U.S. patent application Ser. No. 12/242,353 filed Sep. 30, 2008 and entitled "Methods And Devices For Performing Gastrectomies And Gastroplasties."

Once access to the abdominal cavity is obtained, the surgeon can insufflate the patient's abdominal cavity through an opening in the patient's abdomen, as will be appreciated by a person skilled in the art, to expand the abdominal cavity and provide a larger, more easily navigable surgical workspace. For example, the surgeon can insufflate the abdominal cavity by passing a fluid under pressure, e.g., nontoxic carbon dioxide gas, through the trocar 16. The fluid can have a pressure in the range of about 10 to 15 mm Hg, or any other pressure, as will be appreciated by a person skilled in the art. The trocar 16 can include one more seals that prevent the insufflation fluid from escaping the abdominal cavity through the trocar 16. A non-limiting example of a sealing trocar that does not use seals is the SurgiQuest AirSeal™ available from SurgiQuest, Inc. of Orange, Conn. If one or more openings in addition to the abdominal access hole 12 having the trocar 16 positioned therein are formed through the patient's abdominal wall 14 and have a surgical device, e.g., a trocar, extending therethrough, the device can be configured to provide a seal that prevents the insufflation fluid from escaping the abdominal cavity therethrough.

Figure 4:
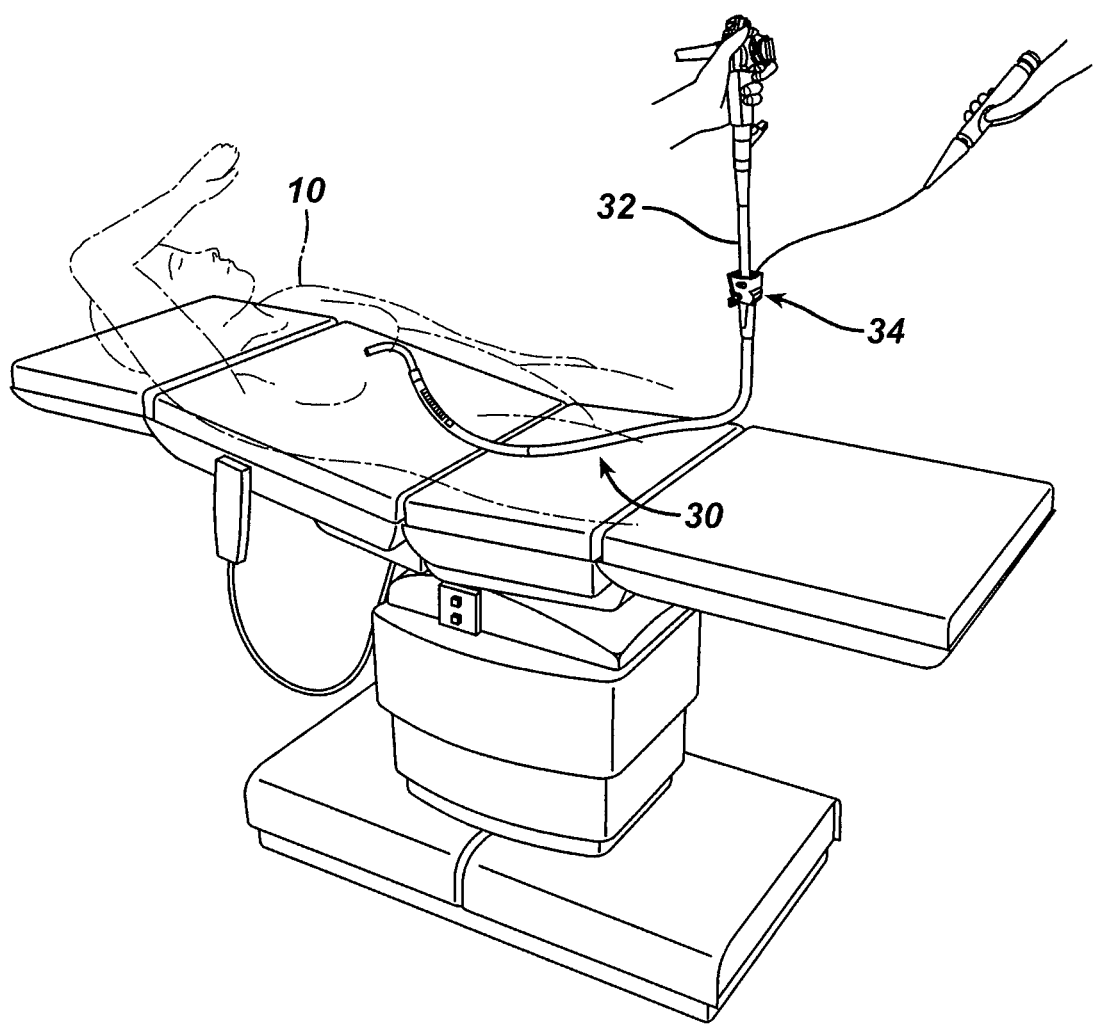
FIG. 4 is a perspective partially transparent view of one embodiment of a patient having an access hole formed in a vaginal wall of the patient.

As shown in FIG. 4, the surgeon can in addition to or instead of one or more abdominal access holes form a vaginal opening or access hole 30 in a vaginal wall of the patient 10 to create an opening between the vagina and the patient's abdominal cavity to gain access to the abdominal cavity. The vaginal access hole 30 can be formed through the vaginal wall in any way, as will be appreciated by a person skilled in the art. In an exemplary embodiment, a trocar 34 can be inserted through the vaginal wall to form the vaginal access hole 30, thereby creating an opening between the vagina and the patient's abdominal cavity.

As mentioned above, a scoping device can be used in the gastroplasty, such as an endoscope 32. The endoscope 32 can be advanced into the vagina before formation of the vaginal access hole 30, and/or it can be advanced through the trocar 34 in the vaginal access hole 30 after formation to provide visualization inside the patient's body during the surgical procedure. The vaginal access hole 30 can be formed before or after the abdominal access hole 12 of FIG. 1, but in an exemplary embodiment, the vaginal access hole 30 is formed after the abdominal access hole 12 to allow prior insufflation of the patient's abdominal cavity through the abdominal access hole 12. Before forming the vaginal access hole 30, as will be appreciated by a person skilled in the art, the patient's vaginal opening can be dilated using a surgical instrument, e.g., a weighted speculum, and/or one or more sutures. The vaginal access hole 30 can have any shape and size, but the vaginal access hole 30 preferably has a diameter of about 18 mm and is configured to allow passage of a surgical instrument, e.g., a trocar, a scoping device, a surgical stapler, a clip applier, etc., having a diameter in a range of about 5 to 18 mm.

During the surgical procedure, the patient's stomach can be difficult to adequately access. The patient's liver can be retracted during the gastroplasty to help the surgeon gain better access to the patient's stomach. Although the liver can be retracted at any time during the surgical procedure, in an exemplary embodiment the liver is retracted after insertion into the patient 10 of a scoping device to provide visualization of the abdominal cavity before and during retraction of the liver. Although visualization before, during, and/or subsequent to liver retraction can be provided using a scoping device that is introduced into the abdominal cavity through an opening in the abdominal wall 14, providing visualization with a vaginally introduced scoping device can allow for increased abdominal work space and/or reduce the "chopstick" effect of abdominally introduced instruments. The liver can be retracted in any way appreciated by a person skilled in the art, but the liver is preferably retracted using at least one device inserted into the abdominal cavity of the patient 10 through, e.g., the previously-formed abdominal access hole 12, through another abdominal opening, through a vaginal access hole, etc. Also as will be appreciated by a person skilled in the art, a draining device, e.g., a penrose drain, a Jackson-Pratt drain, etc., can be disposed in the patient's abdominal cavity to help hold the liver and/or drain excess fluid that can accumulate in the abdominal cavity during the surgical procedure, particularly following liver retraction.

Figure 5:
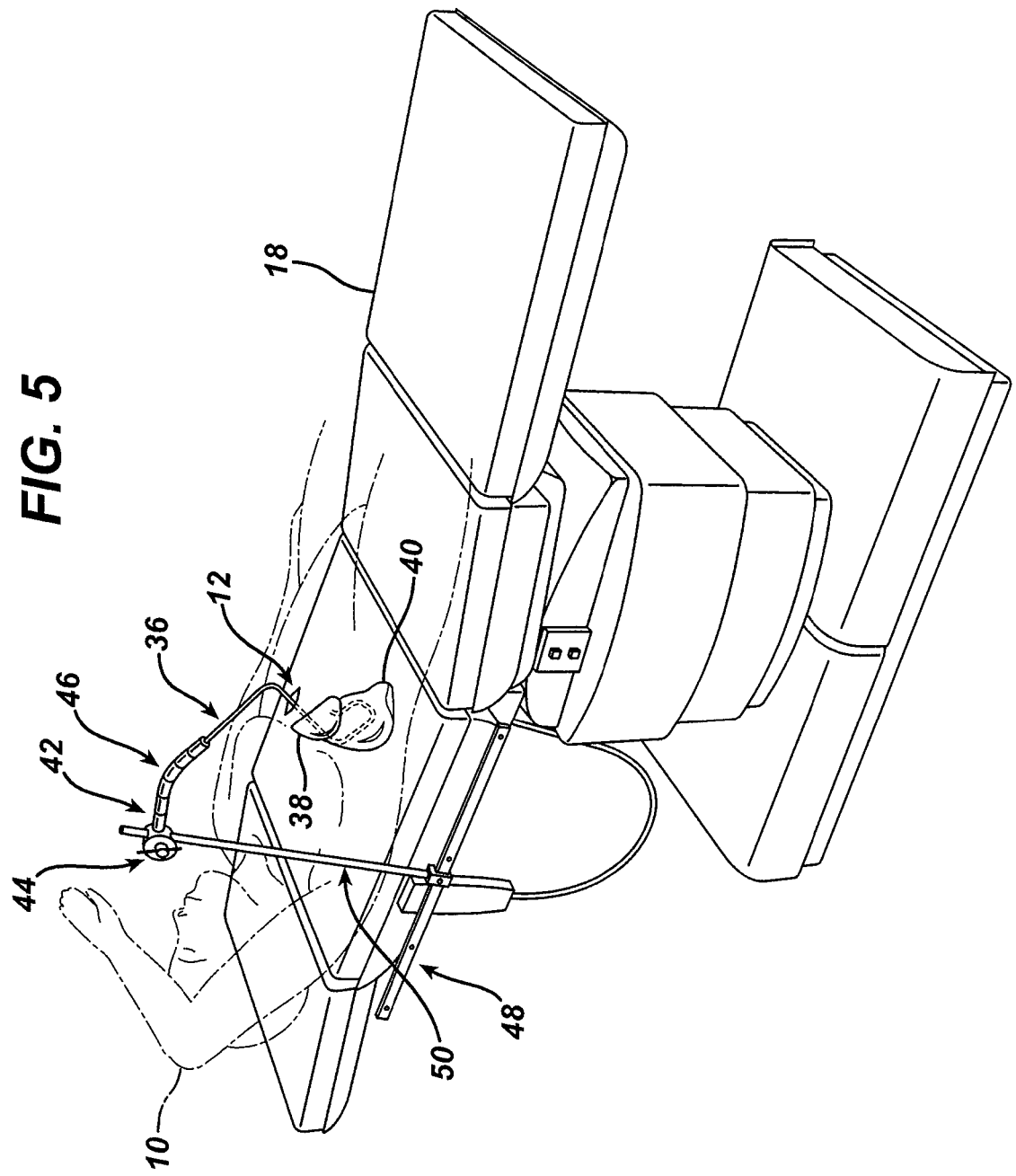
FIG. 5 is a perspective partially transparent view of one embodiment of a liver retracting device retracting a liver of a patient.

In an exemplary embodiment, a retractor device, such as a Nathanson liver retractor, can be used to retract the patient's liver. FIG. 5 illustrates one embodiment of a liver retraction procedure using a Nathanson liver retractor 36 to retract a liver 38 of the patient 10 away from a stomach 40 of the patient 10. As will be appreciated by a person skilled in the art, the surgeon can use the Nathanson liver retractor 36 to "hook" the liver 38 and hold the liver 38 away from the stomach 40 in a desired retracted position. The Nathanson liver retractor 36 can be inserted directly inserted through the abdominal access hole 12 as illustrated, or the Nathanson liver retractor 36 can be advanced through a cannulated device providing access into the patient's abdominal cavity, e.g., through a vaginally inserted trocar, through a multiple port access device, through a sleeve, etc. Although not shown in FIG. 5, the patient's abdominal cavity can be visualized during liver retraction using a scoping device advanced into the patient 10. A grasper (not shown) can be advanced through the abdominal wall 14, e.g., directly, through a multiple port access device 16, through a trocar, via a working channel of a scoping device, etc., to assist in retracting the liver 38 and/or otherwise assist in the gastroplasty.

Optionally, as illustrated in FIG. 5, a support 42 external to the patient 10 can be used to mount the Nathanson liver retractor 36 to the examination table 18 on which the patient 10 rests, although any other support can be used if a support is used at all for a liver retractor. By mounting the Nathanson liver retractor 36, the surgeon does not need to continuously hold the Nathanson liver retractor 36 in place during the surgical procedure, thereby freeing the surgeon to attend to other surgical matters, and/or reducing the required number of operating room personnel. Non-limiting embodiments of a support can be found in previously mentioned U.S. patent application Ser. No. 12/242,333 filed Sep. 30, 2008 and entitled "Methods And Devices For Performing Gastrectomies And Gastroplasties" and U.S. patent application Ser. No. 12/242,353 filed Sep. 30, 2008 and entitled "Methods And Devices For Performing Gastrectomies And Gastroplasties." The support can have a variety of sizes, shapes, and configurations, but as illustrated, the support 42 can include an adapter 44 and a flexible arm 46 configured to couple to the mounted device and configured to be coupled at a terminal end thereof to the adapter 44. The flexible arm 46 is generally configured to be movable, as will be appreciated by a person skilled in the art, to allow the mounted device's position to be adjusted relative to the examination table 18. The adapter 44 can be movable and can mate, as shown, to a table mount coupled to the examination table 18 and including a table rail 48 and a bracket 50 coupled at its respective terminal ends to the table rail 48 and the adapter 44. In an alternate embodiment, in addition to or instead of the examination table 18, the support can mount to another stable structure near the patient 10, e.g., a wall, the ceiling, an independent structure standing on the floor similar to an IV pole or a microphone stand, an overhead fixture, etc. The Nathanson liver retractor 36 can be mounted at any time during the gastroplasty procedure, and its mounting can be re-adjusted and/or released at any time, but in an exemplary embodiment, the Nathanson liver retractor 36 is mounted before arranging the liver 38 into a desired retracted location in the patient 10. The Nathanson liver retractor 36 and/or the support 42, e.g., the flexible arm 46, the adapter 44, and/or the bracket 50, can be adjusted to help move the liver 38 to its desired retracted location.

A person skilled in the art will appreciate that a support can be used to mount the Nathanson liver retractor 36 and/or any other surgical instrument used during the gastroplasty that does not require constant hands-on manipulation. Multiple supports can be used in a single surgical procedure.

Various other non-limiting examples of liver retractor devices and liver retraction methods, such as using a tacker device to apply one or more tacks to the liver and retracting the liver using a device inserted through a multiple port access device, can be found in previously mentioned U.S. patent application Ser. No. 12/242,333 filed Sep. 30, 2008 and entitled "Methods And Devices For Performing Gastrectomies And Gastroplasties," U.S. patent application Ser. No. 12/242,353 filed Sep. 30, 2008 and entitled "Methods And Devices For Performing Gastrectomies And Gastroplasties," and U.S. patent application Ser. No. 12/242,381 filed Sep. 30, 2008 and entitled "Methods And Devices For Performing Gastroplasties Using A Multiple Port Access Device."

Figure 6:
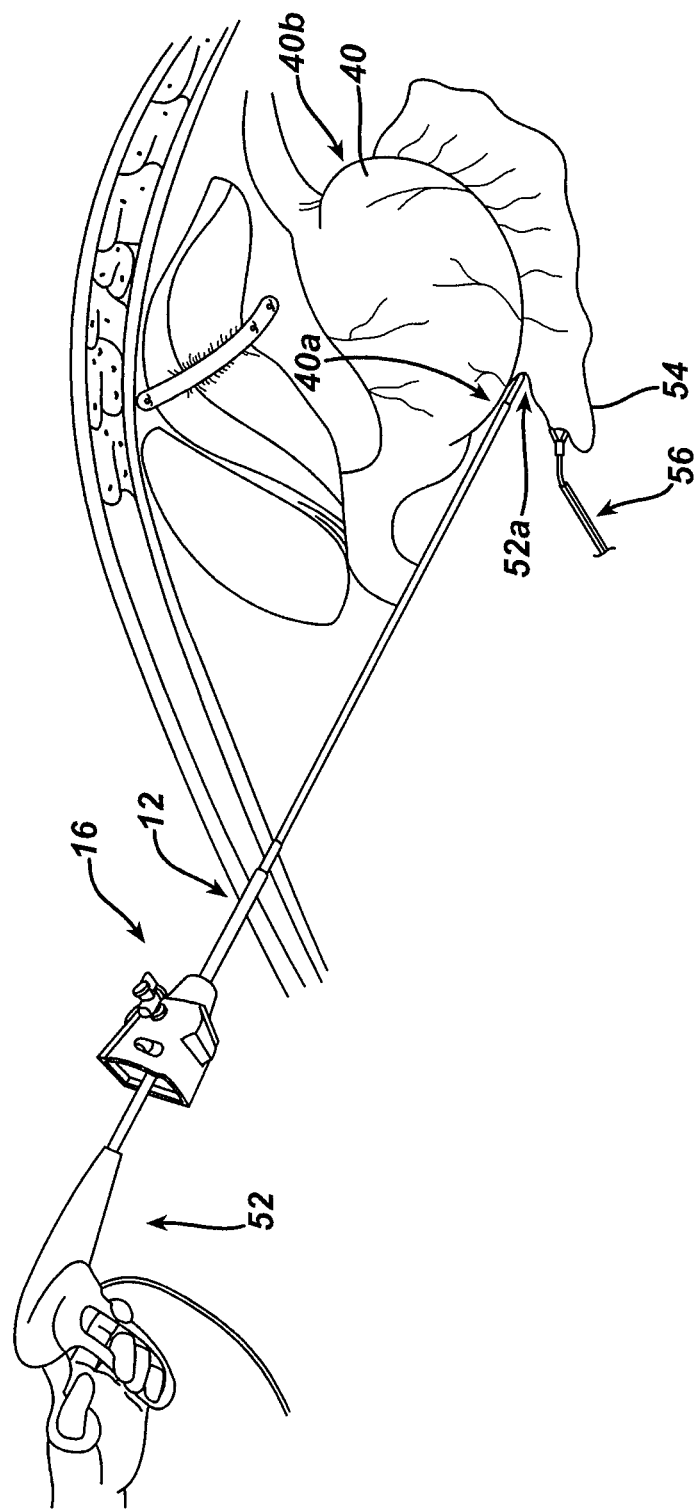
FIG. 6 is a perspective partially transparent view of one embodiment of a dissecting device dissecting tissue from a stomach of a patient.

Prior to transecting the stomach 40, the stomach 40 can be separated from tissue attached to the stomach 40, e.g., an omentum, vessels, any adhesions on the stomach 40, etc., to free a fundus of the stomach 40. As will be appreciated by a person skilled in the art, the tissue attached to the stomach 40 can be separated from the stomach 40 using any one or more dissecting devices. A person skilled in the art will also appreciate that the term "dissector," "dissecting device," or "dissecting surgical instrument" as used herein is intended to encompass any surgical instrument that is configured to cut tissue, e.g., a scalpel, a harmonic scalpel, a blunt dissector, a cautery tool configured to cut tissue, scissors, an endoscopic linear cutter, a surgical stapler, etc. The desired tissue can be separated from the stomach 40 in any way, but in an exemplary embodiment the surgeon cuts adjacent to the greater curvature of the stomach 40 to free the fundus from the omentum. The dissector can be introduced into the patient 40 through any access hole (natural or surgically created). In one embodiment shown in FIG. 6, a dissector 52 can be inserted through the trocar 16 in the abdominal access hole 12 and used to cut an omentum 54 from the stomach 40. As shown in this illustrated embodiment, the dissector 52 has an end effector 52a with a distal end having a pair of movable jaws configured to cut tissue. With the desired tissue dissected, a posterior of the stomach 40 can be visualized and/or accessed between an antrum 40a of the stomach 40 and an angle of His 40b of the stomach 40.

In an exemplary embodiment, the omentum 54 and/or any other desired tissue can be tensioned using a grasper 56 while the dissector 52 dissects tissue from the stomach 40. The grasper 56 can be introduced into the patient 10 in any way, e.g., through a multiple port access device, through a trocar in a percutaneous abdominal opening, through a vaginal access hole, etc. Generally, the surgeon can pass tissue from the dissector 52 to the grasper 56, grasp the tissue with the grasper 56, pull the grasper 56 to tension the grasped tissue, and dissect tissue using the dissector 52. The surgeon can repeat this process any number of times to free the stomach fundus. Although only one grasper is shown in the embodiment illustrated in FIG. 6, the surgeon can use any number of graspers, which can be inserted in any way into the patient's abdominal cavity. If a scoping device is inserted into the patient's abdominal cavity, the surgeon can use the scoping device to provide visualization to, e.g., help position the grasper 56 and/or an additional grasper. Alternatively or in addition, a scoping device can visualize the posterior of the stomach 40 during and/or after dissection of desired tissue.

Figure 7:
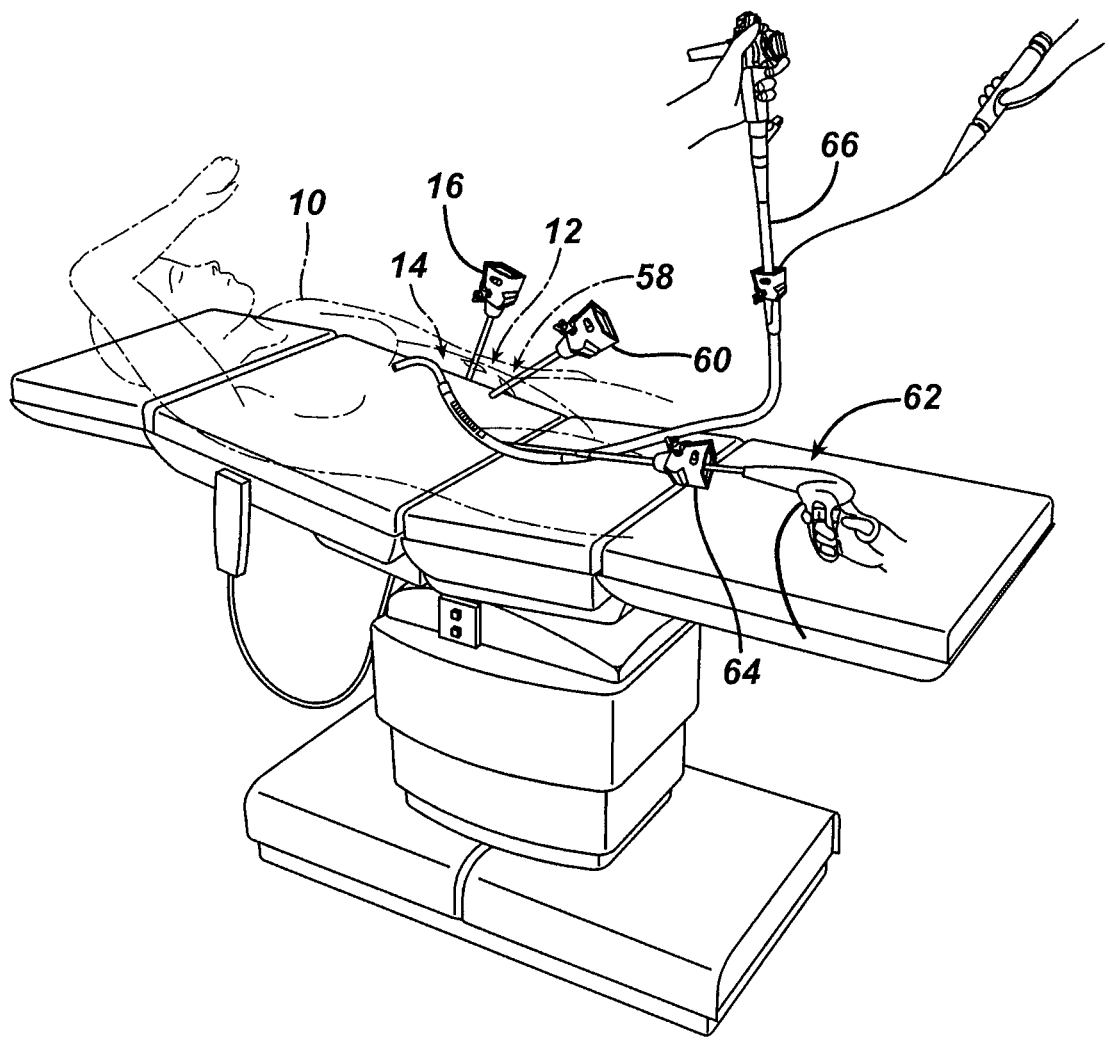
FIG. 7 is a perspective partially transparent view of one embodiment of a vaginally inserted dissecting device dissecting tissue from a stomach of a patient with a grasper tensioning the tissue.

FIG. 7 illustrates an embodiment using multiple graspers where a second abdominal access hole 58, e.g., a percutaneous opening, can be formed using a second trocar 60 similar to that described above regarding the abdominal access holes 12, 26 formed using the trocars 16, 28. The surgeon can insert any one or more desired surgical instruments simultaneously and/or sequentially through the second abdominal access hole 58, with or without the second trocar 60 disposed therein. For non-limiting example only, the surgeon can advance at least one additional grasper through the second abdominal access hole 58 and use the second grasper in cooperation with a grasper 62 inserted through a vaginal trocar 64 to tension the omentum. In some embodiments, the surgeon can use only a grasper inserted through the abdominal wall 14, e.g., through the second abdominal access hole 58, and not a vaginally inserted grasper. Alternatively, the surgeon can advance the additional grasper through another access hole, e.g., the vaginal access hole via a working channel of an endoscope 66, through a multiple port access device inserted in an abdominal or vaginal access hole, etc. In some embodiments, one or more graspers for tensioning the dissected tissue can be inserted through the vaginal access hole, e.g., through a multiple port access device, and none through the patient's abdomen.

Figure 8:
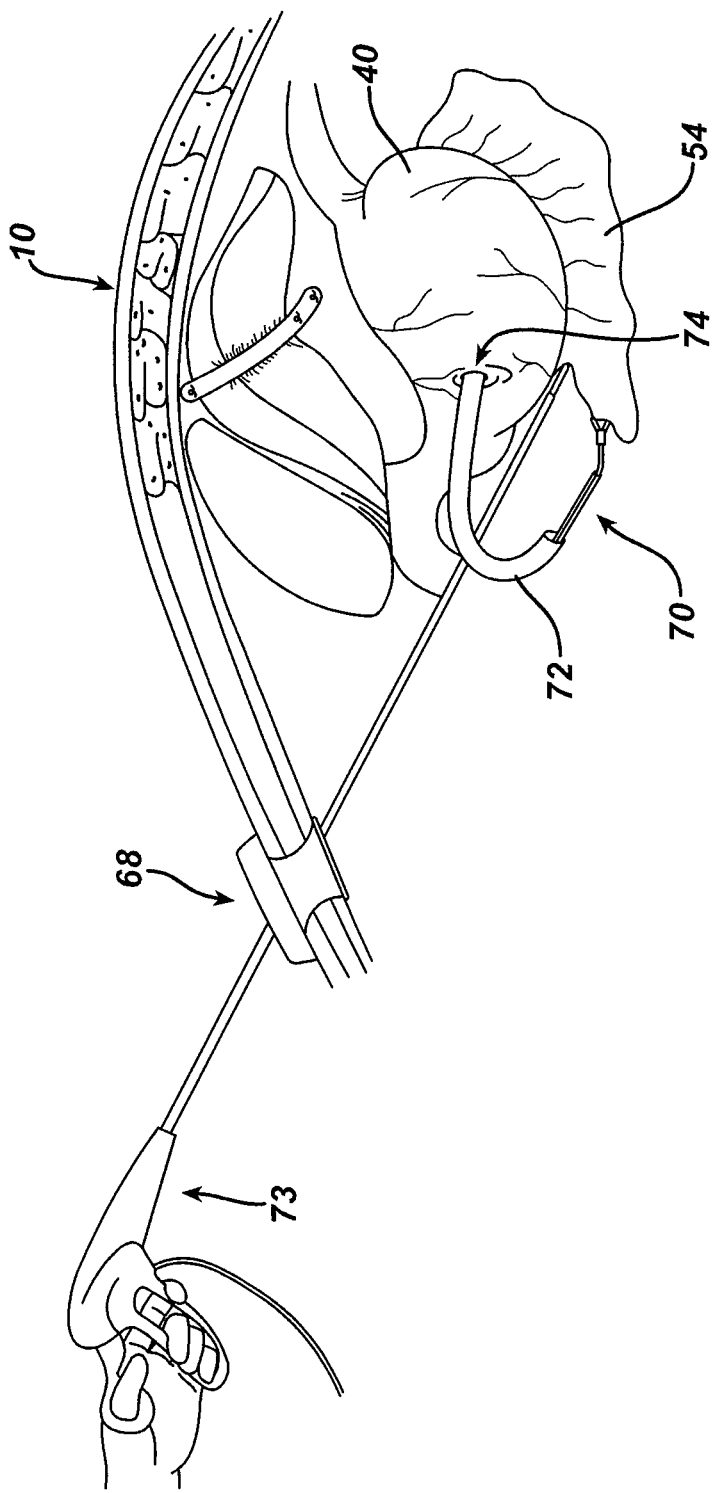
FIG. 8 is a perspective partially transparent view of one embodiment of a dissecting device dissecting tissue from a stomach of a patient with a grasper tensioning the tissue and advanced through an opening in a digestive tract of the patient.

As illustrated in another embodiment in FIG. 8, using a multiple port access device 68 positioned in the patient's abdomen, a dissector 73 can be advanced into the patient 10 and used to dissect the omentum 54. A grasper 70 can be transorally advanced into the stomach 40 through a scoping device 72, advanced through a digestive tract opening 74, and advanced into the abdominal cavity of the patient 10 to grab and tension the omentum 54. The digestive tract opening 74 can be formed in any way appreciated by a person skilled in the art. The digestive tract opening 74 can be formed at any location on the stomach 40, but it is preferably formed in a portion of the stomach 40 that will form part of the stomach sleeve following transection to help maintain constant positioning of any device(s) inserted through the digestive tract opening 74 before, during, and/or after transection. The digestive tract opening 74 is shown formed in the stomach wall, but the digestive tract opening 74 can be formed anywhere in the patient's digestive tract, e.g., in the stomach wall, in an intestine wall, etc. The digestive tract opening 74 can have any shape and size. If the digestive tract opening 74 is not included in a portion of the stomach fundus detached from a remainder of the stomach 40 during transection, the digestive tract opening 74 can be closed in any way appreciated by a person skilled in the art, e.g., using a surgical stapler inserted through an abdominally inserted multiple port access device.

FIG. 9 shows an alternate embodiment using a multiple port access device 76 positioned substantially at an umbilicus of the patient 10 for dissecting tissue attached to the stomach 40. In this illustrated embodiment, the surgeon can use a scoping device advanced through a first one of the multiple port access device's ports 78a, 78b, 78c to visualize the surgical site, a dissector advanced through a second one of the ports 78a, 78b, 78c to dissect the tissue attached to the stomach 40, and a grasper advanced through a third one of the ports 78a, 78b, 78c to tension the tissue being dissected. Alternatively or in addition, a grasper advanced through a trocar 80 inserted through a percutaneous vaginal access hole 82 and/or a grasper advanced through a trocar 84 inserted through a percutaneous abdominal access hole 86 can be used to tension the tissue being dissected. A grasper inserted through at least the percutaneous abdominal access hole 86 can allow tissue to be tensioned in the patient 10 at a transverse angle relative to a surgical instrument, e.g., a cutting instrument, inserted into to the patient 10 through the multiple port access device 76 at the umbilicus.

In some embodiments, an illustrated in one embodiment in FIG. 10, a dissector can be used to form an opening 88 under the stomach 40. The opening 88 can have any size, shape, and configuration, but in the illustrated exemplary embodiment, the opening 88 can include a tunnel having a substantially constant diameter along its longitudinal length and having a substantially circular cross-sectional shape. The surgeon can visualize the posterior of the stomach 40 from the antrum 40a to the angle of His 40b by, e.g., advancing a scoping device through at least a partial longitudinal length of the opening 88. Any dissector can be used to form the opening 88, such as an exemplary dissector described in previously mentioned U.S. patent application Ser. No. 12/242,381 filed Sep. 30, 2008 and entitled "Methods And Devices For Performing Gastroplasties Using A Multiple Port Access Device."

Once tissue attached to the stomach 40 is dissected from the omentum 54 as desired and the opening 88 under the stomach 40 has optionally been formed, the stomach 40 can be transected. As will be appreciated by a person skilled in the art, the stomach 40 can be transected using any one or more transecting devices. A person skilled in the art will also appreciate that the term "transactor," "transecting device," or "transecting surgical instrument" as used herein is intended to encompass surgical devices that alone or in combination can cut and secure tissue, e.g., a surgical stapler configured to cut and staple tissue. Non-limiting embodiments of surgical staplers can be found in U.S. Pat. No. 5,285,945 issued Feb. 14, 1995 and entitled "Surgical Anastomosis Stapling Instrument," U.S. Pat. No. 6,905,057 issued Jun. 14, 2005 and entitled "Surgical Stapling Instrument Incorporating A Firing Mechanism Having A Linked Rack Transmission," U.S. Pat. No. 7,111,769 issued Sep. 26, 2006 and entitled "Surgical Instrument Incorporating An Articulation Mechanism Having Rotation About The Longitudinal Axis," U.S. Pat. No. 6,786,382 issued Sep. 7, 2004 and entitled "Surgical Stapling Instrument Incorporating An Articulation Joint For A Firing Bar Track," U.S. Pat. No. 6,981,628 issued Jan. 3, 2006 and entitled "Surgical Instrument With A Lateral-Moving Articulation Control," U.S. Pat. No. 7,055,731 issued Jun. 6, 2006 and entitled "Surgical Stapling Instrument Incorporating A Tapered Firing Bar For Increased Flexibility Around The Articulation Joint," U.S. Pat. No. 6,964,363 issued Nov. 15, 2005 and entitled "Surgical Stapling Instrument Having Articulation Joint Support Plates For Supporting A Firing Bar," U.S. Pat. No. 6,959,852 issued Nov. 1, 2005 and entitled "Surgical Stapling Instrument With Multistroke Firing Incorporating An Anti-Backup Mechanism," U.S. Pat. No. 7,434,715 issued Oct. 14, 2008 and entitled "Surgical Stapling Instrument Having Multistroke Firing With Opening Lockout," U.S. Pat. No. 7,000,819 issued Feb. 21, 2006 entitled "Surgical Stapling Instrument Having Multistroke Firing Incorporating A Traction-Biased Ratcheting Mechanism," and U.S. Pat. No. 7,364,061 issued Apr. 29, 2008 and entitled "Surgical Stapling Instrument Incorporating A Multistroke Firing Position Indicator And Retraction Mechanism," which are hereby incorporated by reference in their entireties.

The transactor can have any size and shape, but in an exemplary embodiment if the transactor is vaginally advanced into the patient 10, the transactor preferably has a relatively long longitudinal length, e.g., at least about 4 feet, and has at least one flexible joint. Non-limiting embodiments of a transactor having at least one flexible joint can be found in previously mentioned U.S. patent application Ser. No. 12/242,381 filed Sep. 30, 2008 and entitled "Methods And Devices For Performing Gastroplasties Using A Multiple Port Access Device." A person skilled in the art will also appreciate that the transactor can be inserted into the patient 10 through any opening, e.g., through an abdominal access hole, a vaginal access hole, a natural orifice, etc., with or without a trocar or multiple port access device positioned therein. Further, at least one grasper inserted through any opening(s) in the patient 10 can be used to tension the stomach 40 while it is being transected and/or to hold a sizer in a desired location along the stomach's lesser curvature.

In an exemplary embodiment, the transactor can be configured to cut tissue and to deliver one or more fasteners to tissue. In particular, the transactor can have at its distal end an end effector configured to engage tissue. The end effector can have a cut-free region such that the transactor can cut tissue engaged in a first portion, e.g., distal portion, of the end effector without cutting tissue engaged in a second portion, e.g., proximal portion, of the end effector. The end effector can also have a fastener-free region, which can be substantially at the same location as the cut-free region, such that the device can fasten tissue engaged in the distal portion of the end effector without fastening tissue in the end effector's proximal portion. A device having a proximal cut-free region, and/or a proximal fastener-free region substantially at the same location as the proximal cut-free region, can be particularly effective in a Magenstrasse and Mill procedure where only a portion of the stomach 40 is cut to form a stomach sleeve. Such a device can be used to at least begin a transection with the device engaging the stomach 40 at a portion of its perimeter and transecting at least a portion of the stomach 40 a distance from the stomach's antrum 40*a* without cutting through the engaged portion of the stomach's perimeter. Exemplary transectors will be discussed in more detail below.

Figure 11:
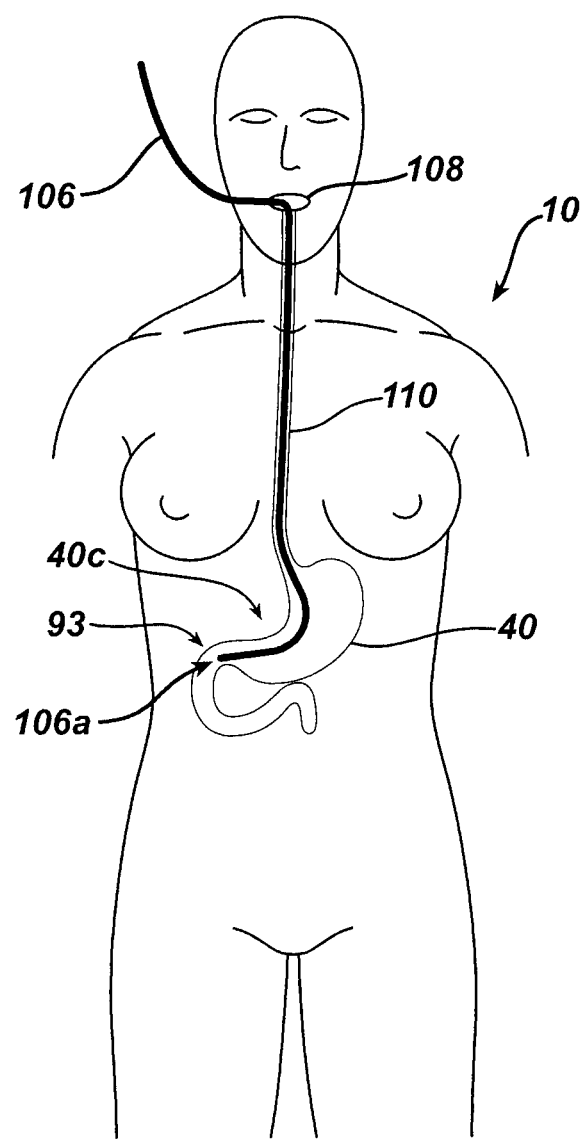
FIG. 11 is a perspective partially transparent view of one embodiment of a sizer advanced into a stomach of a patient.

At any time prior to transecting the stomach 40, the surgeon can manipulate the stomach 40 to form a gastric tube or stomach sleeve in the stomach 40. In an exemplary embodiment, the stomach sleeve can be formed after creation of the tunnel 88 under the stomach 40 and an opening created through anterior and posterior walls of the stomach 40, as discussed further below, although the sleeve can be formed before or after creation of the tunnel 88 or the opening. As illustrated in FIG. 11, the surgeon can introduce a sizing device 106 into the stomach 40 to help size the portion of the stomach 40 that will form the stomach sleeve. The sizing device 106 can be introduced into the stomach 40 in any way, but in this illustrated exemplary embodiment, the sizing device 106 is transorally introduced into the stomach 40, e.g., through a mouth 108 and an esophagus 110 of the patient 10. A person skilled in the art will appreciate that the term "sizer," "sizing device," or "sizing instrument" as used herein is intended to encompass any surgical instrument, e.g., a bougie, a scoping device, a catheter, etc, that is configured to indicate a desired gastric sleeve area. The sizer 106 can optionally include a light at its distal end to help the surgeon advance the sizer 106 through the esophagus 110 and desirably position the sizer 106 in the stomach 40. The sizer's size and shape can generally correspond to a size and shape of the stomach sleeve desired to be formed in the patient 10, so the surgeon can choose a sizer having any size, shape, and configuration that generally corresponds to the desired sleeve dimensions. In an exemplary embodiment, the sizer 106 is a flexible surgical instrument having a substantially cylindrical shape and a substantially constant diameter along the sizer's longitudinal length in the range of about 28 to 42 French (about 9.3 to 14 mm).

The sizer 106 can be adjusted in the stomach 40 to place the sizer 106 in a sizing position that generally indicates the size and position of the stomach sleeve following at least partial transection of the stomach 40. In an exemplary embodiment, the sizer 106 in the sizing position extends along a lesser curvature 40*c* of the stomach 40 and into a pylorus 93 of the stomach 40 so at least a distal-most end 106*a* of the sizer 106 extends to the pyloric sphincter or valve of the pylorus 93. The sizer 106 can be adjusted in the patient 10 in any way, as will be appreciated by a person skilled in the art. In an exemplary embodiment, the sizer 106 can be adjusted in the stomach 40 using a flexible and/or rigid grasper inserted into the stomach 40 through an abdominal access hole. The grasper can include an end effector having two opposed, movable jaws configured to grasp and move the sizer 106 once the sizer 106 has been adequately advanced into the patient 10 for the grasper to access it. A scoping device inserted into the stomach 40 can have a light located thereon which can help the surgeon find and grasp the sizer 106 with the grasper and to locate the pyloric valve. As mentioned above, if the sizer 106 is advanced into the stomach 40 before the opening is created, the sizer's positioning along the lesser curvature 40*c* can assist in the opening's creation.

Figure 12:
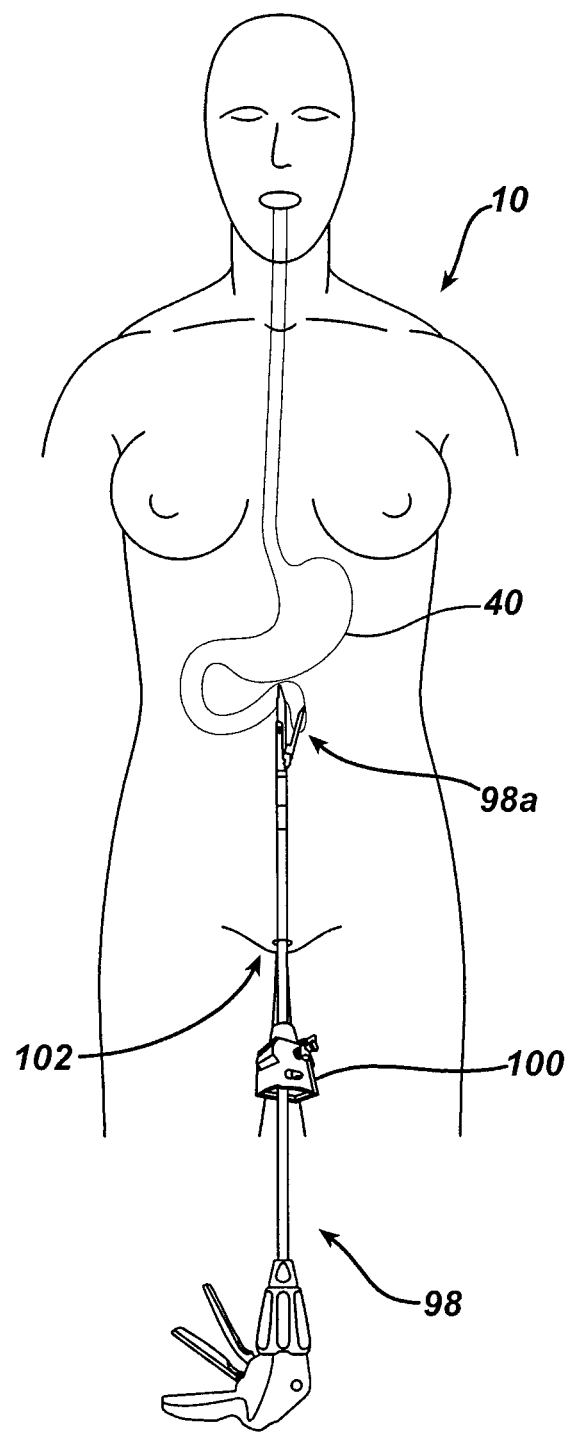
FIG. 12 is a perspective partially transparent view of one embodiment of a transecting device transecting a stomach of a patient and inserted into the patient through an access hole formed in a vaginal wall of the patient.
Figure 13:
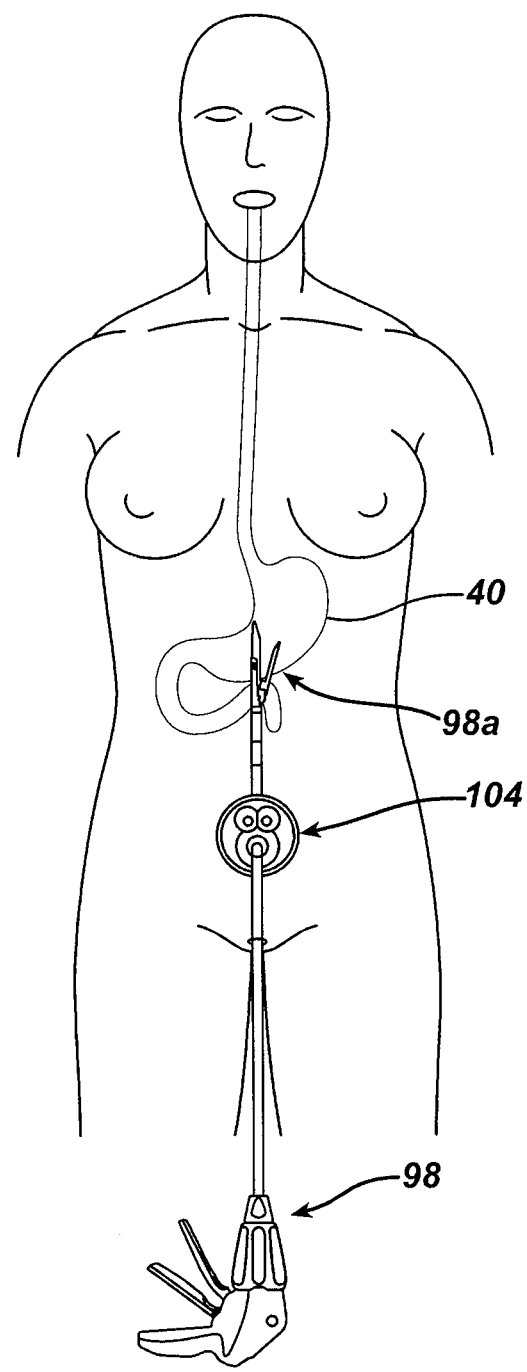
FIG. 13 is a perspective partially transparent view of one embodiment of a transecting device transecting a stomach of a patient and inserted into the patient through a multiple port access device disposed in an abdomen of the patient.

As mentioned above, a transector can be introduced into the patient 10 in any way, such as by advancing a transactor 98 having an end effector 98*a* in the form of opposed jaws through a trocar 100 inserted in a vaginal access hole 102, as shown in one embodiment in FIG. 12. In another embodiment illustrated in FIG. 13, the surgeon can transect the stomach 40 using the transecting device 98 advanced through a multiple port access device 104 positioned in the patient's umbilicus. The transection can be visualized using at least one scoping device inserted through any opening, as discussed herein. For non-limiting example only, visualization of the stomach 40 above and/or underneath the stomach 40 can be performed using, e.g., a scoping device inserted through the trocar 16 in the abdominal access hole 12 of FIG. 1, to determine if a desired path of transection is clear or readily cleared of tissue and/or other debris. For another non-limiting example, one scoping device can be used for visualization before the transection, e.g., a scoping device inserted through the trocar 16 in the abdominal access hole 12 of FIG. 1, and another scoping device during and after the transection, e.g., a vaginally introduced scoping device. The stomach 40 can optionally be tensioned during transection. For example, a suture can be passed through a percutaneous opening, e.g., through a trocar or other port, and the suture can be inserted through the fundus of the stomach 40 and back out the stomach 40 and out the percutaneous port. The free ends of the suture can thus be tensioned to lift and stretch the stomach 40, thereby facilitating transection. The surgeon can also place one or more draining devices in the stomach fundus following the transection, e.g., along a greater curvature of the stomach sleeve formed by the transection. If used, the sizer can be removed from the stomach 40 at any time during the surgical procedure, but in an exemplary embodiment the sizer is removed from the patient 10 by retracting it through the patient's mouth, if the sizer was transorally introduced, after the stomach 40 has been transected and inspected via scoping device visualization for any uncorrected and potentially dangerous irregularities, e.g., improperly bent staples, improperly placed staples, untied sutures, etc.

Figure 14:
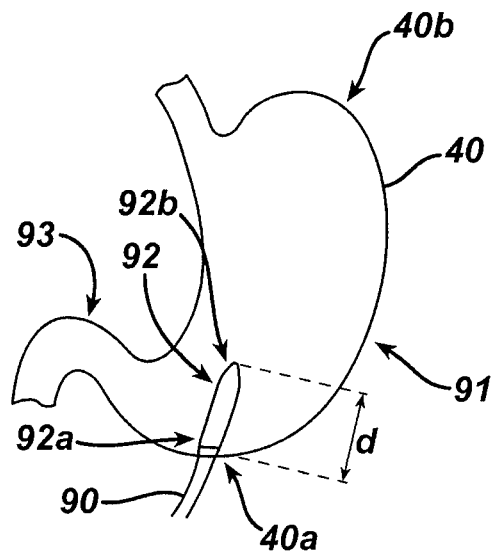
FIG. 14 is a perspective view of one embodiment of a transecting device positioned in an initial position to transect a portion of a stomach of a patient.

However advanced to the stomach 40, in an exemplary embodiment shown in FIG. 14, a transector 90, e.g., a linear surgical stapler having an end effector 92 at a distal end thereof, can be used to engage a portion of the stomach 40 and at least begin transection of the stomach 40 by cutting and/or fastening a portion of the tissue engaged by the end effector 92. The end effector 92 can be initially positioned at any location with respect to the stomach 40 before the transector 90 transects the stomach 40, but in an exemplary embodiment, the transactor 90 can be positioned in an initial position with a proximal end 92*a* of the end effector 92 located substantially at the antrum 40*a* of the stomach 40 and with a distal end 92*b* of the end effector 92 located a distance d from the antrum 40*a* toward the angle of His 40*b*. Thus, in the initial position the end effector 92 can engage a folded edge of the stomach 40 at the antrum 40*a*. If an opening or tunnel has been formed under the stomach 40, e.g., the opening 88 of FIG. 10, the opening can help provide guidance for positioning the end effector 92 in its initial position. In some embodiments, as discussed further below, the end effector 92 can have a longitudinal length such that the distal end 92*b* of the end effector 92 extends beyond the angle of His 40*b* when its proximal end 92*a* is positioned substantially at the antrum 40*a* such that the transector 90 can form a stomach sleeve without being substantially repositioned from its initial position.

As mentioned above, the surgeon can use a surgical instrument such as a scoping device to visualize the posterior and/or other area of the stomach 40. Such visualization can help determine the initial position of the transecting device 90 relative to the stomach 40. Initial positioning of the transector 90 can be determined in any way, as will be appreciated by a person skilled in the art. For example, a distance can be measured along a greater curvature 91 of the stomach 40 from the pylorus 93 of the stomach 40, and in an exemplary embodiment from a pyloric sphincter or valve of the pylorus 93, to determine an initial position for the distal end 92b of the end effector 92. In an exemplary embodiment, the initial position for the distal end 92b of the end effector 92 has a lateral distance from the pylorus 93 in a range of about 2 to 6 centimeters (cm) and has an axial distance from the antrum 40a of about 2 cm. The size of the end effector 92 can generally determine its initial position, particularly if a sizer is used to provide a guide for positioning of the stomach sleeve to be formed. The end effector 92 can simply be positioned to engage the antrum 40a with its distal end 92b positioned along the stomach 40 toward the angle of His 40b. Alternatively or in addition, the initial position for the distal end 92b of the end effector 92 can be marked in any way, such as by mentally marking or remembering the initial position for the end effector's distal end 92b or by applying a marker. As will be appreciated by a person skilled in the art, any marker can be used to mark the initial position for end effector's distal end 92b, e.g., a mark using electrocautery, a mark using a harmonic scalpel, an ink marker applied in any way appreciated by a person skilled in the art, such as via a marking device inserted through an abdominal or other access hole, etc.

Figure 15:
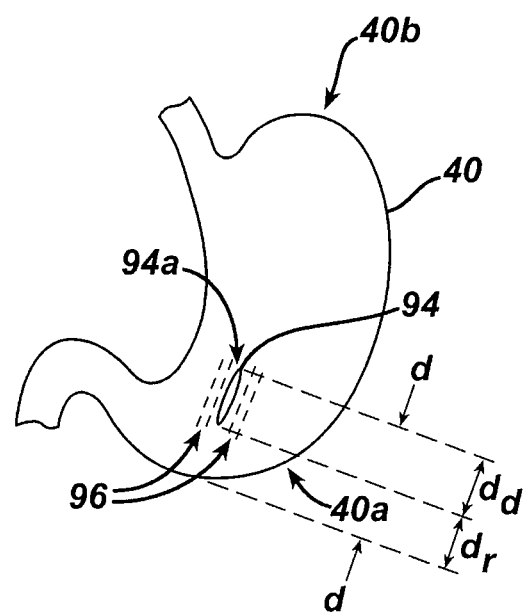
FIG. 15 is a perspective view of one embodiment of a sealed opening formed by the transecting device of FIG. 14.

With the transector 90 engaging the stomach 40, the transecting device 90 can be actuated in any way appreciated by a person skilled in the art to cut the stomach 40 and to create a hole or opening 94 through anterior and posterior walls of the stomach 40, as shown in FIG. 15. The opening 94 can have a terminal end 94a approximately the distance d from the antrum 40a toward the angle of His 40b, e.g., substantially where the end effector's distal end 92b was positioned to form the opening 94. The opening 94 can more easily allow a transection device, either the transector 90 or one or more other transectors, to be desirably positioned with respect to the stomach 40 to transect the remainder of the stomach 40 between the opening 94 and the angle of His 40b, as discussed further below. The opening 94 can have any size and shape, e.g., substantially circular, etc. Generally, a longitudinal length $d_d$ of the opening 94 can correspond to a longitudinal length of the distal cutting region of the transector's end effector 92, while an uncut longitudinal length $d_p$ of the stomach 40 extending between a perimeter or folded edge of the stomach 40 at the antrum 40a and the opening 94 can correspond to a longitudinal length of the proximal cut-free region of the transector's end effector 92. The opening 94 can be closed or sealed to help prevent bleeding and/or prevent fluid or debris seepage between the stomach 40 and the patient's abdominal cavity. Having a closed opening can also provide the surgeon with increased flexibility during the surgical procedure because the surgeon can create the opening 94 without immediately transecting the stomach 40 thereafter but instead first, e.g., size the stomach 40. The opening 94 can be closed in any way, as will be appreciated by a person skilled in the art, such as by applying one or more fasteners or securing elements, e.g., staples 96 as shown applied by the transector 90, sutures, glues such fibron glues, pledgets, etc. The securing element(s) can be applied following creation of the opening 94, and/or the transactor 90 can be configured to apply one or more securing elements when it forms the opening 94, e.g., by applying the staples 96 from a distal portion of the end effector 92 but not from a proximal portion of the end effector 92.

Figure 16:
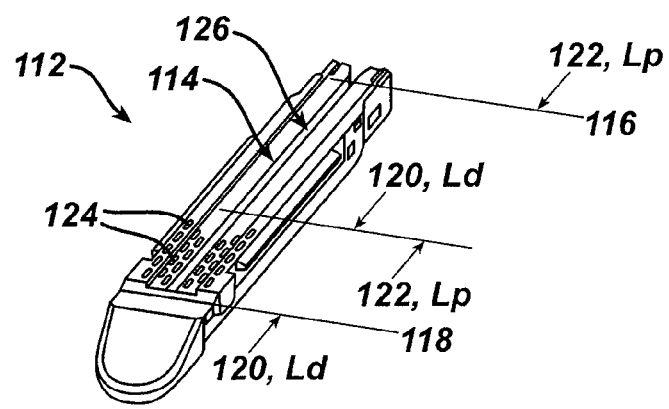
FIG. 16 is a perspective view of one embodiment of a staple cartridge having a proximal, cut-free and fastener-free region.
Figure 17:
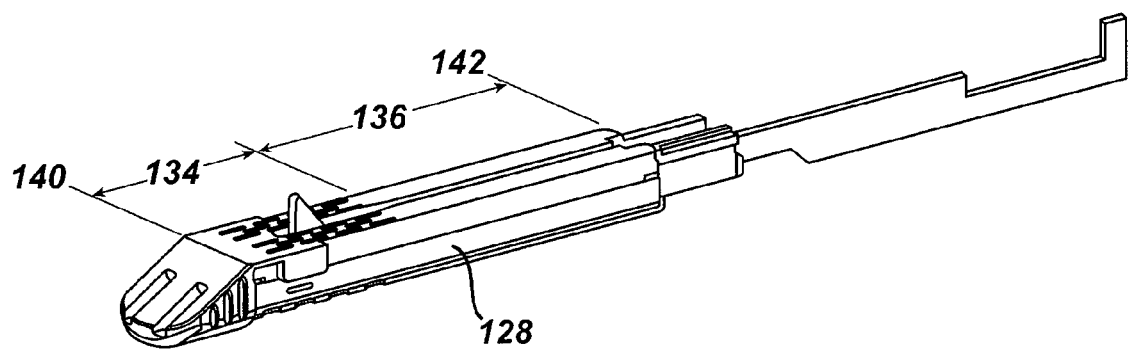
FIG. 17 is a perspective view of one embodiment of a cutting assembly coupled to a staple cartridge having a proximal, cut-free and fastener-free region.
Figure 18:
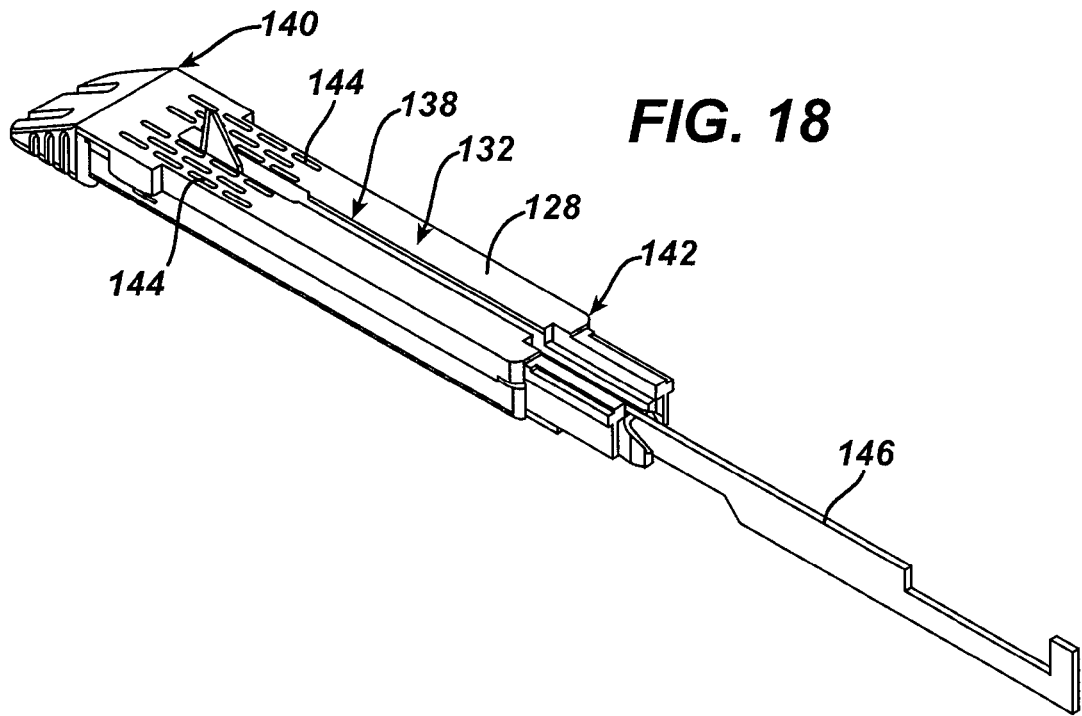
FIG. 18 is another perspective view of the cutting assembly and staple cartridge of FIG. 17.
Figure 19:
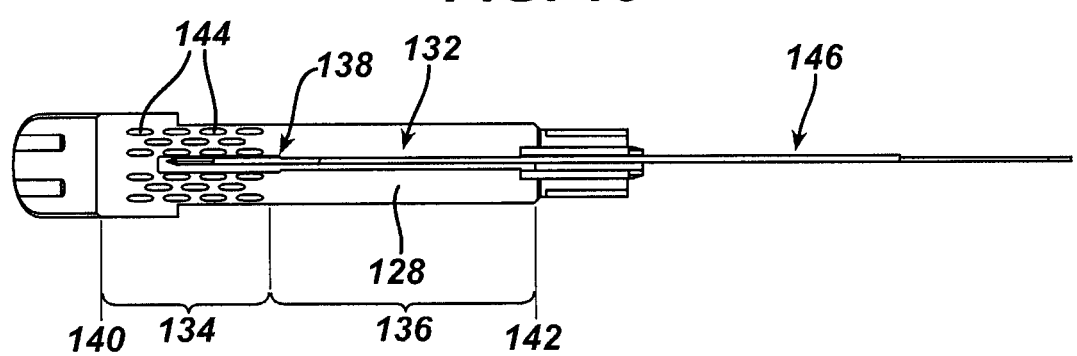
FIG. 19 is a top view of the cutting assembly and staple cartridge of FIG. 17.
Figure 20:
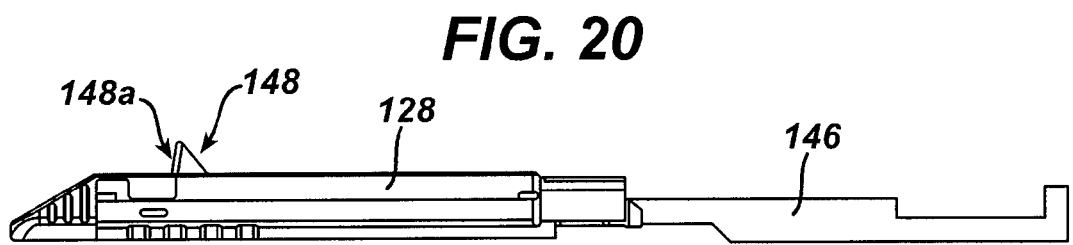
FIG. 20 is a side view of the cutting assembly and staple cartridge of FIG. 17.

A transector having a cut-free region and/or a fastener-free region can have a variety of configurations. FIG. 16 illustrates one embodiment of a staple cartridge 112 having a proximal cut-free and fastener-free region. The staple cartridge 112 is configured to be removably and replaceably disposed in one of two movable jaws of an end effector of a transector. A person skilled in the art will appreciate that while the transactor in this illustrated embodiment is configured to apply surgical staples, a transector can be configured to apply any type of fastener to secure tissue. A person skilled in the art will also appreciate that although FIG. 16 illustrates a removable cartridge 112 that can be loaded into any transection device, e.g., the transactor 98 of FIGS. 12 and 13, need not include a cartridge but rather be a single-use device having the fasteners disposed directly therein. In other embodiments, various portions of the transector can be removable and replaceable, such as the entire end effector or the cutting element.

As shown in FIG. 16, the staple cartridge 112 can have a substantially planar tissue-contacting surface 114 on one side thereof. As will be appreciated by a person skilled in the art, when the cartridge 112 is disposed in an end effector of a transection device and tissue is engaged by opposed jaws of the end effector, tissue can be pressed against the tissue-contacting surface 114 between proximal and distal ends 116, 118 of the tissue-contacting surface 114. The cartridge 112 can be configured so that tissue engaged adjacent the tissue-contacting surface 114 in a distal region 120 of the cartridge 112 and adjacent a tissue-contacting surface of a jaw opposed to the jaw containing the cartridge 112, e.g., an anvil, can be cut and stapled without cutting and stapling tissue engaged adjacent the tissue-contacting surface 114 in a proximal region 122 of the cartridge 112. The distal and proximal regions 120, 122 can each extend along any portion of the longitudinal length of the cartridge 112, but in an exemplary embodiment, the proximal region 122 has a longitudinal length Lp at least as long as a longitudinal length Ld of the distal region 120, e.g., has a longitudinal length Lp in a range of about 10% to 70% of a total length (Lp+Ld) between the proximal and distal ends 116, 118, e.g., at least about 20%. The total length between the proximal and distal ends 116, 118 can vary, but in an exemplary embodiment, the total length is in a range of about 60-180 mm, with the proximal region 122 having a length Lp in a range of about 30-90 mm.

The cartridge's distal region 120 can generally be configured to cut and staple tissue in any way appreciated by a person skilled in the art. The proximal region 122 can also have a variety of configurations to prevent tissue engaged adjacent thereto from being cut or stapled. To help fasten tissue, the distal region 120 can include a plurality of staple holes 124 in which staples can be loaded for deployment into tissue. The proximal region 122 can, as shown, not include such staple holes and instead can have a substantially continuous solid surface along the tissue-contacting surface 114. In this way, if a staple driver longitudinally translates through the cartridge 112 to eject staples therefrom, staples can be driven into tissue in the distal region 120 while no staples will be driven from the proximal region 122. Indeed, staples need not be loaded into the proximal region 122 at all. In other embodiments, the proximal region 122 can have holed but staples can only be loaded in the distal region 120 and not in the proximal region 122 to form a proximal staple-free region.

To help cut tissue, the cartridge 112 can include a longitudinal slot 126 extending at least through the distal region 120, or through both the distal and proximal regions 120, 122 as shown in this illustrated embodiment. A cutting element, e.g., a knife having a sharp cutting edge, can translate along the longitudinal slot 126 to cut tissue engaged adjacent the distal region 120 without cutting tissue adjacent the proximal region 122, as discussed further below. Generally, the cutting element can translate along a full or partial length of the cartridge 112 between the proximal and distal ends 116, 118 in the distal and/or proximal regions 120, 122. If the cutting element moves along only a partial length of the longitudinal length between the proximal and distal ends 116, 118, the partial length can include the length of the distal region 120 to allow the cutting element to cut tissue in the distal region 120. A person skilled in the art will appreciate that the knife can have a variety of sizes, shapes, and configurations and that its sharp cutting edge can extend along any portion of the knife's perimeter. A person skilled in the art will also appreciate that the cutting element can also translate through a corresponding longitudinal slot in a jaw opposed to the cartridge 112, e.g., a slot in an anvil.

FIGS. 17-22 partially illustrate a second embodiment of a transector having a proximal cut-free and fastener-free region where tissue engaged adjacent the proximal region is not cut or fastened. In this illustrated embodiment, a transector component that can be partially or fully removably and/or fixedly attached to any transection device includes a staple cartridge 128 and a cutting assembly 130. As will be appreciated by a person skilled in the art, the staple cartridge 128 and the cutting assembly 130 can each have a variety of configurations and can each include more or fewer elements than those shown. The cartridge 128 is similar to the cartridge 112 of FIG. 16 and has a tissue-contacting surface 132, a distal cutting/fastening region 134, a proximal cut-free/fastener-free region 136, and a longitudinal slot 138 extending between distal and proximal ends 140, 142 of the tissue-contacting surface 132 through which at least a portion of the cutting assembly 130 can at least partially translate. Generally, staples can be disposed in staple holes 144 formed in the cartridge's tissue-contacting surface 132 and ejected into tissue engaged adjacent the distal region 134. The cartridge 128 includes six longitudinal rows of staple holes 144, three on either side of the slot 138, although the staple holes 144 can be in any number and can be arranged in any way.

Figure 21:
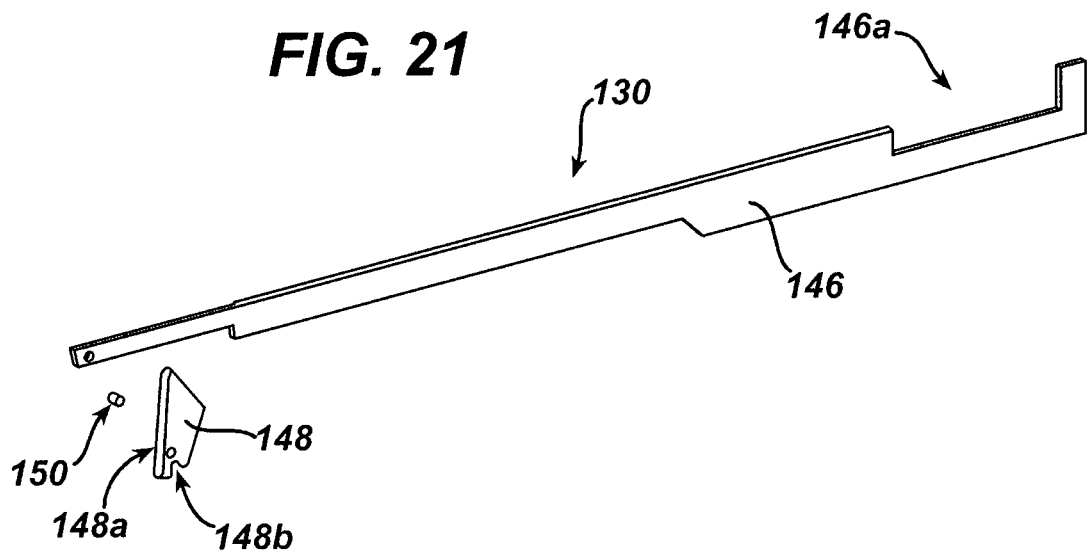
FIG. 21 is an exploded view of the cutting assembly of FIG. 17.
Figure 22:
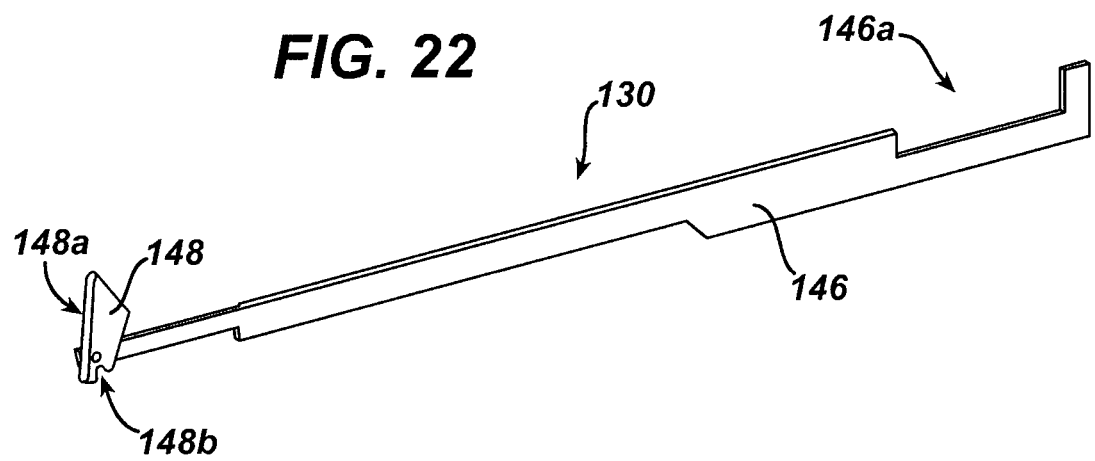
FIG. 22 is a perspective view of the cutting assembly of FIG. 17 with a cutting element of the cutting assembly in a cutting position.
Figure 23:
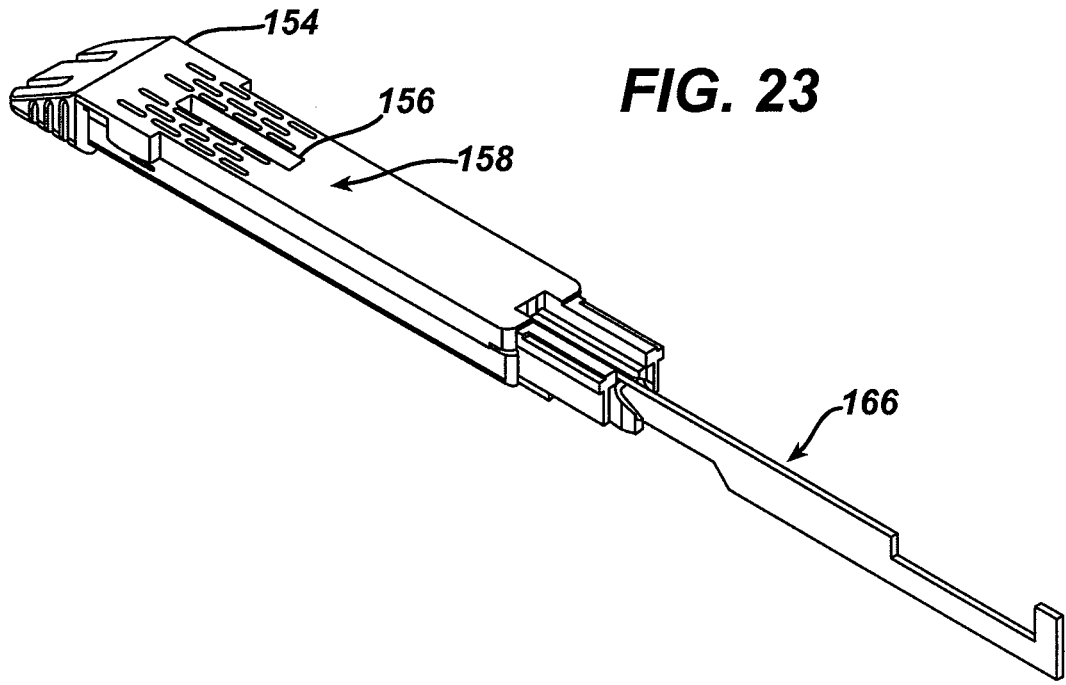
FIG. 23 is a perspective view of another embodiment of a cutting assembly coupled to a staple cartridge having a proximal, cut-free and fastener-free region.
Figure 24:
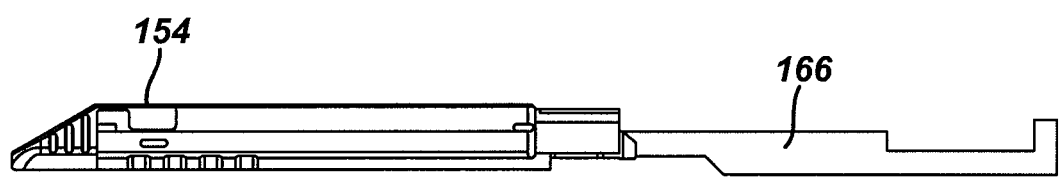
FIG. 24 is a side view of the cutting assembly and staple cartridge of FIG. 23.
Figure 25:
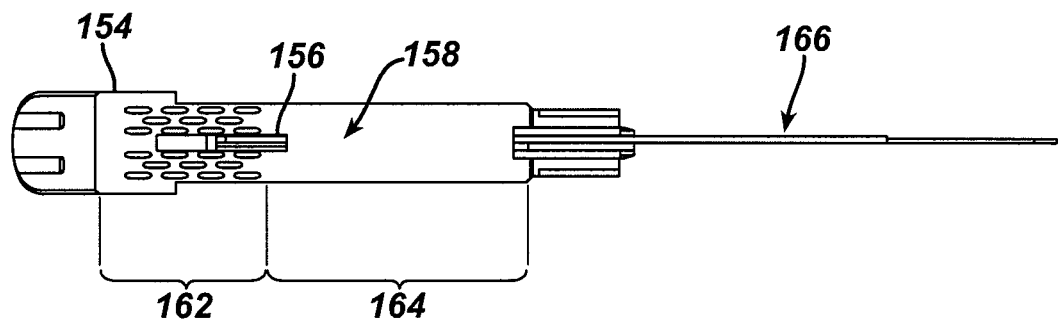
FIG. 25 is a top view of the cutting assembly and staple cartridge of FIG. 23.

The cutting assembly 130 includes a pusher bar 146 and a cutting element, e.g. a knife 148, pivotably attached to a distal end of the pusher bar 146 with, e.g., a pin 150 shown in FIG. 21. A person skilled in the art will appreciate that the knife 148 can connect to the pusher bar 146 with any other connecting element configured to allow the knife 148 to rotate relative to the pusher bar 146, e.g., pin-welding, brazening, soldering, an integrated tab or semi-perforations from material used to form the knife 148, etc. The knife 148 can, as shown, have a distal cutting edge 148*a* and a proximal cut-out 148*b* on a side of the knife 148 opposite to the cutting edge 148*a*. With a distal cutting edge 148*a*, the knife 148 can cut tissue when the knife 148 moves distally, as discussed further below. The pusher bar 146 can be attached to an actuation mechanism (not shown), e.g., a handle assembly, at a proximal portion 146*a* of the pusher bar 146, where the actuation mechanism can be configured to move the cutting assembly 130 relative to the cartridge 128. A person skilled in the art will appreciate that the knife and the fasteners can be actuated in any way using any handle and/or other actuation mechanism. The knife 148 can rotate about the pin 150 relative to the pusher bar 146 and to the cartridge 128 coupled to the cutting assembly 130, as discussed further below. In this way, when the knife 148 moves through the cartridge 128, the knife 148 can move between a first position configured to not cut tissue in the proximal region 136 and a second position configured to cut tissue in the distal region 134. A person skilled in the art will appreciate that the pin 150 and at least a distal portion of the pusher bar 146 can each also move through the cartridge 128.

The knife 148 is shown in FIGS. 17-20 and 22 attached to the pusher bar 146 in a cutting position where the knife 148 is in a position configured to cut tissue engaged by the transactor. Accordingly, the knife 148 can be in the cutting position in the distal region 134. In the cutting position, at least a portion of the knife 148 including at least a portion of the cutting edge 148*a* can extend outside the longitudinal slot 138 and above the tissue-contacting surface 132. A person skilled in the art will appreciate that "above" is a relative position indicating that the knife 148 extends through the cartridge's tissue-contacting surface 132 toward an opposed tissue-contacting surface (not shown) against which tissue can be engaged such that tissue can be clamped between the two tissue-contacting surfaces. The opposed tissue-contacting surface, such as that of an anvil, can have any configuration as will be appreciated by a person skilled in the art.

In a third embodiment of a transector having a proximal cut-free and fastener-free region illustrated in FIGS. 23-28, a staple cartridge 154 has a longitudinal slot 156 extending through the cartridge 154 but extending through a tissue-contacting surface 158 of the cartridge 154 along only a partial longitudinal length thereof in the cartridge's distal cutting/fastening region 162. The cartridge 154 is otherwise similar to the staple cartridges discussed above with the distal cutting/fastening region 162 and a proximal cut-free/fastener-free region 164. At least a portion of a cutting assembly 160 can at least partially extend through the slot 156 as the cutting assembly 160 moves through the cartridge 154. By having a slot 156 in the distal region 162 but not in the proximal region 164, the cutting assembly 160 cannot extend through the slot 156 to cut tissue except in a distal region 162. Because the tissue-contacting surface 158 in the proximal region 164 can be a continuous solid surface without having any openings formed therein, the cutting assembly 160 cannot access tissue in the proximal region 164 of the tissue-contacting surface 158, thereby helping to ensure that tissue in the proximal region 164 is not cut.

Figure 26:
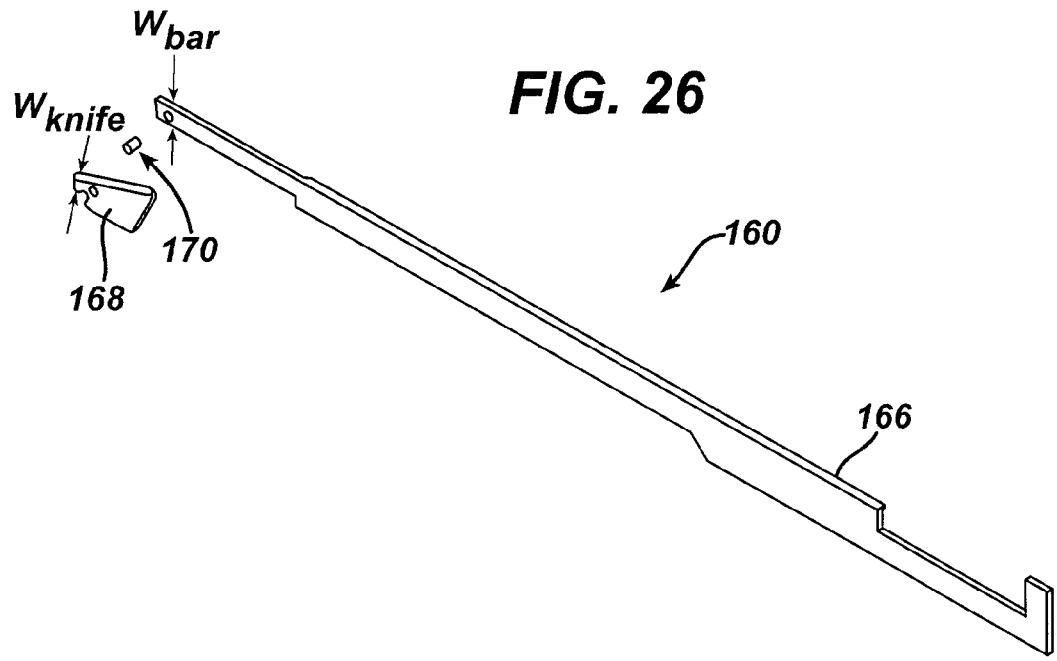
FIG. 26 is an exploded view of the cutting assembly of FIG. 23.
Figure 27:
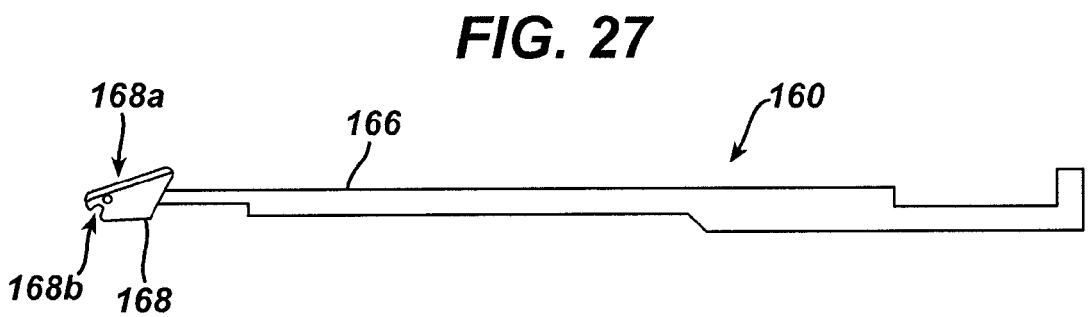
FIG. 27 is a side view of the cutting assembly of FIG. 23 with a cutting element of the cutting assembly in an initial, non-cutting position.
Figure 28:
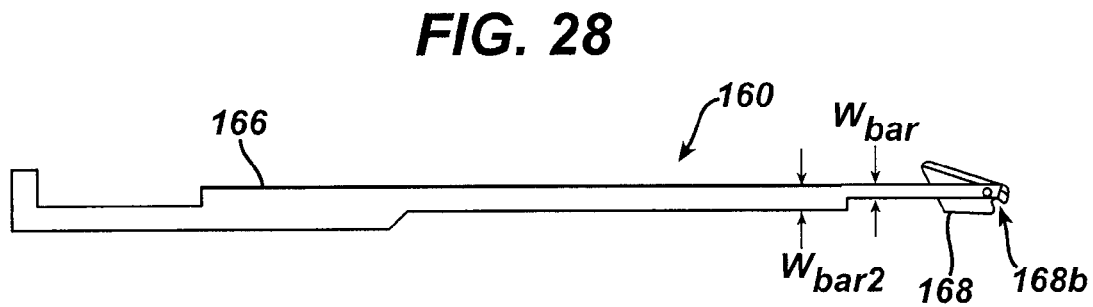
FIG. 28 is another side view of the cutting assembly of FIG. 23 with the cutting element in the initial, non-cutting position.

The cutting assembly 160 of FIGS. 26-28 is similar to the cutting assembly 130 of FIGS. 17-22 discussed above and has a pusher bar 166 and a cutting element, e.g., a knife 168 having a distal cutting edge 168*a* and a cut-out 168*b*, attached to the pusher bar 166 with a pin 170. The distal cutting edge 168*a* extends along an entire length of the knife's distal side, although the cutting edge can, in some embodiments, extend along a partial length of the knife's side. The knife 168 is illustrated in FIGS. 27 and 28 a non-cutting position where the knife 168 is configured to not cut tissue adjacent the tissue-contacting surface 158. Accordingly, the knife 168 can be in the non-cutting position in the proximal region 164. In the non-cutting position, the cutting edge 168*a* of the knife 168 can be contained within the cartridge 154 when the knife 168 translates through at least a portion thereof such that the cutting edge 168*a* does not extend "above" the tissue-contacting surface 158. The position of the knife 168 in the non-cutting position relative to the pusher bar 166 can position the knife's cut-out 168*b* at a distal end of the cutting assembly 160, as shown in FIGS. 27 and 28. In this way, as discussed further below, a cam member can engage the cut-out 168*b* when the cutting assembly 160 moves distally, thereby camming or moving the knife 168 from the non-cutting position to a cutting position. The pusher bar 166 at its distal end can have a width w$_{bar}$ no greater than a width w$_{knife}$ of the knife 168 to help prevent the pusher bar 166 from interfering with the cam member's engagement of the knife's cut-cut 168b. The cut-out 168b can have any size and shape, such as a having a c-shape as illustrated in this embodiment.

As mentioned above, the cutting element in a transection device can have a variety of configurations, and it can be configured to move between different positions as it translates through the transection device's end effector. In some embodiments, the cutting element can move distally through the transactor to cut tissue, while in other embodiments the cutting element can move proximally through the transactor to cut tissue. Generally, if the cutting element moves distally through the transactor to cut tissue, the cutting element has a distal cutting edge and is disposed in the transector in an initial position adjacent or proximal to the distal, cutting region of the transector's end effector to allow the cutting element to cut all tissue engaged in the distal region. Similarly, if the cutting element moves proximally through the transactor to cut tissue, the cutting element has a proximal cutting edge and is disposed in the transector in an initial position adjacent or distal to the distal, cutting region of the transector's end effector to allow the cutting element to cut all tissue engaged in the distal region.

One embodiment of a transector having a cutting element that moves distally to cut is illustrated in FIGS. 29-32. The cutting assembly of FIGS. 23-28 is shown in FIGS. 29-32 moving through the staple cartridge 154. The cutting assembly can move through at least a partial length of the slot 156 in the cartridge 154 with the knife 168 in an initial, non-cutting position, shown in FIG. 29, where the knife 172 is configured to be fully contained within the cartridge 154 to help prevent the knife 168 from cutting tissue adjacent the cartridge 154. The knife 168 can be configured to be in the initial position in the proximal, cut-free region 164 of the cartridge 154 and to move to a second, cutting position in the distal, cutting region 162 of the cartridge 154. In an exemplary embodiment, the knife 168 can be configured to move through an entire length of the proximal region 164 in the initial, non-cutting position and through an entire length of the distal region 162 in the cutting position.

Figure 29:
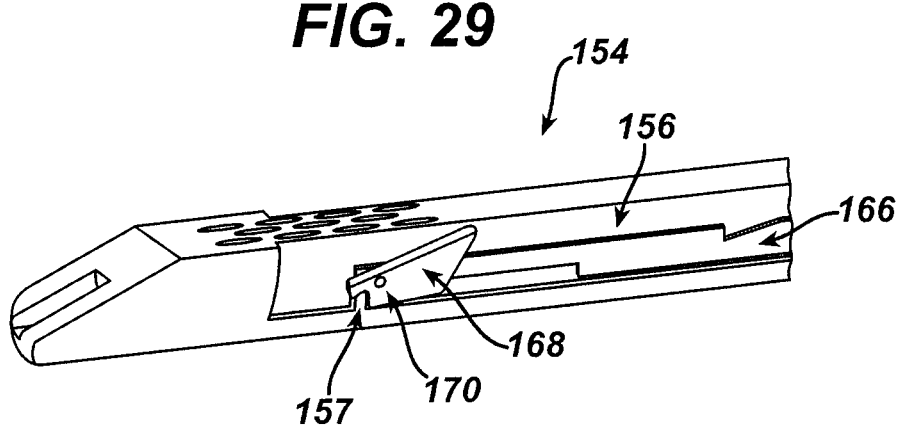
FIG. 29 is a partial cutaway perspective view of the cutting assembly and staple cartridge of FIG. 23 with the cutting element in an initial, non-cutting position and engaging a cam member in the staple cartridge.
Figure 30:
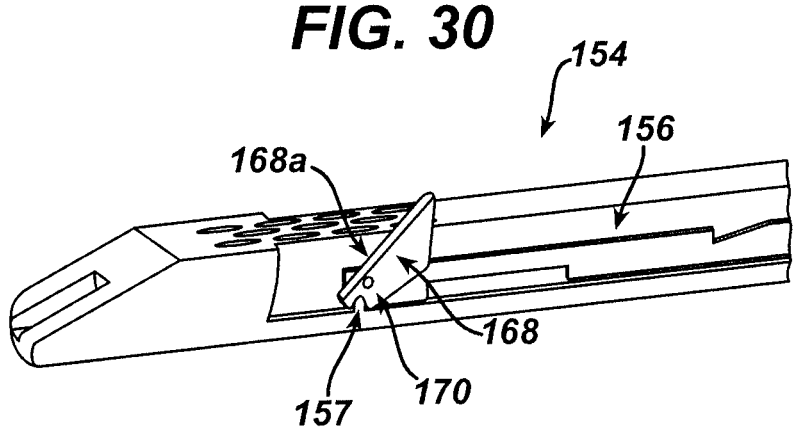
FIG. 30 is a partial cutaway perspective view of the cutting element of FIG. 29 rotating around the cam member from the initial, non-cutting position to a cutting position.

The knife 168 can move between the non-cutting and cutting positions in a variety of ways, but as shown in this illustrated embodiment, a bottom surface of the cartridge's longitudinal slot 156 can include a surface feature, e.g., a cam member 157, to help move the knife 168 between its non-cutting and cutting positions. The cam member 157 can be integrally formed with the cartridge 154, although in other embodiments the cam member 157 can be an independent element fixedly or removably coupled to the cartridge 154 or to the jaw of the transector. The cam member 157 can have any size and shape. As shown in this illustrated embodiment, the cam member 157 has a size and shape corresponding to a size and shape of the cut-out 168b in the knife 168, e.g., c-shaped. In this way, the cut-out 168b can receive the cam member 157 therein when the cut-out 168b reaches the cam member 157 in the knife's translation through the slot 156, as shown in FIG. 29, and can use the cam member 157 as leverage to rotate the knife 168 around the pin 170 in a counter-clockwise direction as the cutting assembly moves distally, as shown in FIG. 30. Because the pin 170 that attaches the knife 168 to the pusher bar 166 can be positioned such that the knife's pivot point at the pin 170 is located "above" the cam member 157 with the knife 168 in the initial position, the knife 168 can have adequate leverage to rotate around the pin 170 relative to the pusher bar 166 as the knife 168 continues its distal movement past the cam member 157.

As the knife 168 rotates around the pin 170 with the cam member 157 received in the knife's cut-out 168b, the knife's cutting edge 168a can move from its containment within the cartridge 154 to extend at least partially outside the cartridge 154 through the opening of the slot 156 in the distal region 162.

Figure 31:
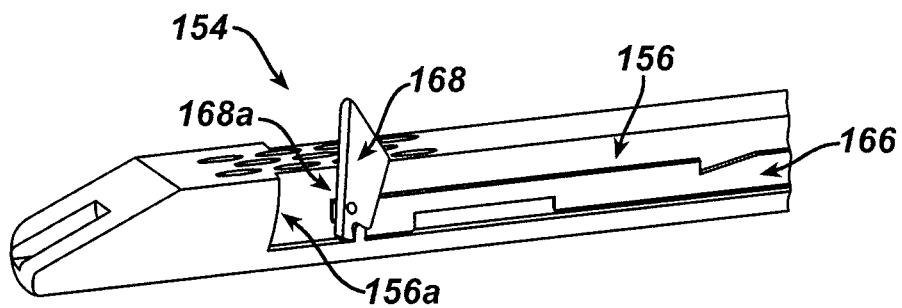
FIG. 31 is a partial cutaway perspective view of the cutting element of FIG. 30 in the cutting position rotated around the cam member.

The knife 168 can cut tissue adjacent the tissue-contacting surface 158 when it is rotated from the non-cutting position to the cutting position, as shown in FIG. 31, with the cutting edge 168a of the knife 168 extending through the longitudinal slot 156 above the tissue-contacting surface 158. The knife 168 in the cutting position can be rotated any amount from the non-cutting position, but as illustrated in this exemplary embodiment, the knife 168 can rotate about 90° from the non-cutting position to the cutting position. Accordingly, the knife 168 in the cutting position in the cartridge's distal region 162 can be configured to cut tissue adjacent the tissue-contacting surface 158 using the knife's cutting edge 168a facing distally. A person skilled in the art will appreciate that the knife 168 can begin to cut tissue as the knife 168 transitions between the non-cutting and cutting positions before the knife 168 has fully moved about 90° to the cutting position. Tissue engaged by the transector can provide adequate tension to hold the knife 168 in the cutting position during distal translation of the knife 168.

Figure 32:
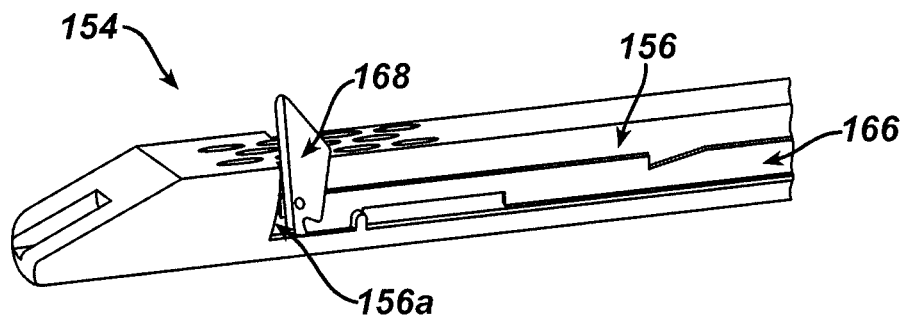
FIG. 32 is a partial cutaway perspective view of the cutting element of FIG. 31 distally advanced in the cartridge in the cutting position.

The cutting assembly can be configured to move distally in the cartridge 154 beyond the cam member 157 with the knife 168 in the cutting position until a stop member prevents further distal movement of the cutting assembly. The stop member can have a variety of configurations as will be appreciated by a person skilled in the art. As shown in this illustrated embodiment, a distal edge 156a of the slot 156 forms the stop member. When a distal-most end of the cutting assembly, e.g., the knife's cutting edge 168a, contacts the slot's distal edge 156a, the distal edge 156a can halt the cutting assembly's distal movement, as shown in FIG. 32.

A second embodiment of a transector having a cutting element that moves distally is illustrated in FIGS. 33-36. The cutting assembly includes a knife 172 attached to a pusher bar 178 with a pin 180. The cutting assembly can be configured to move through a longitudinal slot 182 formed in a staple cartridge 184 and, at least when the knife 172 is in a cutting position, the knife 172 can be configured to move through a corresponding longitudinal slot (not shown) formed in an anvil 186. The cartridge 184 and the anvil 186 form an end effector of the transactor, with the cartridge 184 and the anvil 186 being located on opposed jaws configured to clamp tissue therebetween in a tissue gap 176, as will be appreciated by a person skilled in the art. The knife 172 has a distal cutting edge 174.

Figure 33:
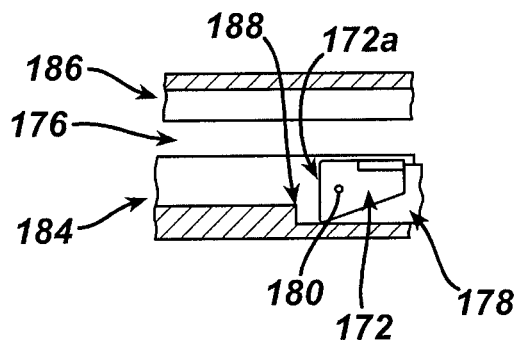
FIG. 33 is a partial cutaway side view of one embodiment of a cutting assembly coupled to an end effector having a proximal, cut-free and fastener-free region and including a staple cartridge and an anvil, with a cutting element of the cutting assembly in an initial, non-cutting position.
Figure 34:
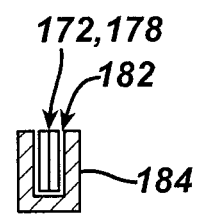
FIG. 34 is a partial cutaway end view of the cutting assembly and the staple cartridge of FIG. 33.
Figure 35:
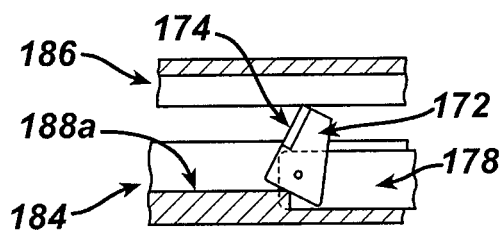
FIG. 35 is a partial cutaway end view of the cutting assembly of FIG. 33 distally translating through the staple cartridge with a cutting element of the cutting assembly moving from the initial, non-cutting position to a cutting position.

In an initial, non-cutting position shown in FIG. 33, the knife 172 is configured to be fully retained within and to distally translate through the cartridge 184 in an initial position without cutting tissue engaged between the anvil 186 and the cartridge 184 in the tissue gap 176. The knife 172 can be configured to be in the initial position in a proximal, cut-free region of the cartridge 184 and to move to a second, cutting position in a distal, cutting region of the cartridge 184. The knife 172 can move between the non-cutting and cutting positions in a variety of ways, but as shown in this illustrated embodiment, a bottom surface of the cartridge's longitudinal slot 182 can include a surface feature, e.g., a camming edge or lip 188, to help move the knife 172 between its non-cutting and cutting positions. The lip 188 can have a substantially 90° angle as illustrated in this embodiment, or the lip 188 can have a non-90° curve or slope to help more smoothly transition the knife 172 over the lip 188. In the cartridge's proximal region, the slot 182 can have a depth in the cartridge 184 that is greater than a depth in the cartridge's distal region by a depth d1. In this way, when the cutting assembly distally moves through the slot 182 with the knife 172 in the initial position, a bottom edge 172*a* of the knife 172 can contact the lip 188. Because the pin 180 that attaches the knife 172 to the pusher bar 178 can be positioned such that the knife's pivot point is located "above" the lip 188 with the knife 172 in the initial position, the knife 172 can have adequate leverage to rotate around the pin 180 in a counter-clockwise direction relative to the pusher bar 178 and to the end effector as the knife 172 continues its distal movement past the lip 188 through the end effector, as shown in FIG. 35.

Figure 36:
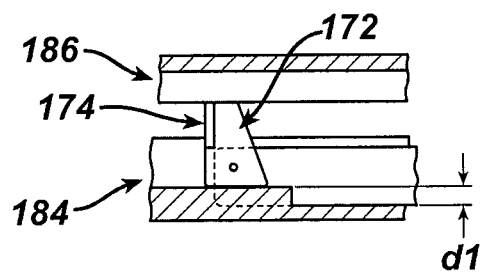
FIG. 36 is a partial cutaway end view of the cutting assembly of FIG. 34 distally translating through the staple cartridge with the cutting element in the cutting position.

After rotating from the non-cutting position to the cutting position, as shown in FIG. 36, the bottom edge 172*a* of the knife 172 can initially move through the longitudinal slot 182 along a lip edge 188*a* forming a bottom surface of the slot 182 in the cartridge's distal, cutting region. The lip edge 188*a* can retain the knife 172 in its cutting position as it translates distally. Accordingly, the knife 172 in the cutting position in the cartridge's distal region can be configured to cut tissue in the tissue gap 176 using the knife's now distally facing cutting edge 174. The pusher bar 178 can be configured to accommodate the different depths of the longitudinal slot 182 by having a smaller width in its distal region than at least in an intermediate region adjacent the distal region, e.g., $w_{bar}$ being less than $w_{bar2}$ as shown in the pusher bar 166 of FIG. 28, such that the pusher bar 178 can move through the cartridge 184 without interfering with any tissue in the tissue gap 176 even after the knife 172 distally passes the lip 188.

If the cutting assembly is pulled proximally after the knife 172 has contacted the lip 188 and at least started to rotate around the pin 180 or move along the lip edge 188*a*, the knife 172 in the cutting assembly as illustrated can move back to its non-cutting position from the cutting position proximally past the lip 188. Depending on the material used to form the knife 172 and the type of tissue clamped in the tissue gap 176, the tissue in the tissue gap 176 can provide adequate tension and resistance to move the knife 172 from the cutting position to the non-cutting position when the knife 176 is pulled proximally past the lip 188, e.g., into the proximal, cut-free region, because the tissue located proximally past the lip 188 has not been cut and can thus act as a cam member. Optionally, the cutting assembly can include a rotation mechanism (not shown), e.g., a rotation spring, a return contact formed in a wall of the cartridge 184 in the slot 182, etc., configured to move the knife 172 from the cutting position to the non-cutting position when the knife 172 is moved proximally beyond the lip 188.

A third embodiment of a transector having a cutting element that moves distally to cut is illustrated in FIGS. 37-40. The cutting assembly includes a pusher bar 190 having a knife 192 formed at a distal end of the pusher bar 190. Similar to the cutting assembly of FIGS. 33-36, the cutting assembly can be configured to move through a longitudinal slot 196 formed in a staple cartridge 198 and, at least when the knife 192 is in a cutting position, the knife 192 can be configured to move through a corresponding longitudinal slot (not shown) formed in an anvil 200. The knife 192 can be integrally formed with the pusher bar 190 and connected to a main body 190*a* of the pusher bar 190 via a flexible hinge 194 as shown. The flexible hinge 194 can be formed from the same material as the main body 190*a* and the knife 192, which is preferably rigid to provide adequate support to the pusher bar 190 as it moves distally and/or proximally. To make the rigid material of the pusher bar 190 flexible, the area of the pusher bar 190 forming the hinge 194 can be treated to become flexible in any way appreciated by a person skilled in the art, e.g., with heat treatment, with scoring, etc. In an alternate embodiment illustrated in FIG. 41, a knife 192' can be an independent element coupled to a pusher bar 190' via a flexible connector element 191 having any configuration and connected to the pusher bar 190' and the knife 192' in any way as will be appreciated by a person skilled in the art, e.g., a wire spot welded to opposed slots formed in the pusher bar 190' and the knife 192'. The knife 192' can move between positions when the connector element 191 bends, similar to the knife 192 moving between positions when the hinge 194 bends, as discussed further below. A person skilled in the art will appreciate that the flexible connector element 191 can be mated to the hinge 194 to provide the hinge 194 with additional structural support.

Figure 37:
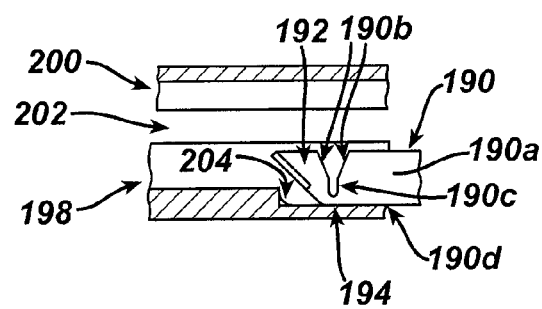
FIG. 37 is a partial cutaway side view of another embodiment of a cutting assembly coupled to an end effector having a proximal, cut-free and fastener-free region and including a staple cartridge and an anvil, with a cutting element of the cutting assembly in an initial, non-cutting position.
Figure 38:
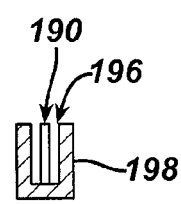
FIG. 38 is a partial cutaway end view of the cutting assembly and the staple cartridge of FIG. 37.
Figure 39:
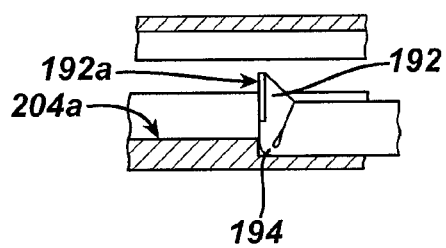
FIG. 39 is a partial cutaway end view of the cutting assembly of FIG. 37 distally translating through the staple cartridge with a hinge of the cutting assembly bending to move the cutting element from the initial, non-cutting position to a cutting position.
Figure 40:
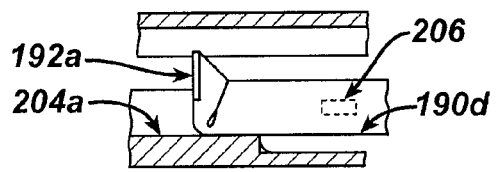
FIG. 40 is a partial cutaway end view of the cutting assembly of FIG. 39 distally translating through the staple cartridge with the cutting element in the cutting position.
Figure 41:
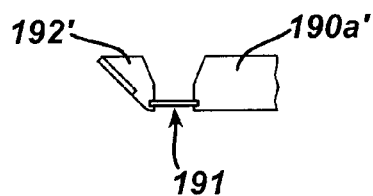
FIG. 41 is a partial side view of one embodiment of a cutting assembly having a cutting element coupled to a pusher bar with a flexible connector element.

Referring again to the embodiment of FIGS. 37-40, in an initial, non-cutting position shown in FIG. 37, the knife 192 can be configured to be fully retained within the cartridge 198 such that the knife 192 can distally translate through the cartridge 198 in the initial position without cutting tissue engaged between the anvil 200 and the cartridge 198 in the tissue gap 202. The knife 192 can be configured to be in the initial position in a proximal, cut-free region of the cartridge 198 and to move to a second, cutting position in a distal, cutting region of the cartridge 198. The knife 192 can move between the non-cutting and cutting positions in a variety of ways, but as shown in this illustrated embodiment, a bottom surface of the cartridge's longitudinal slot 196 can include a surface feature, e.g., a camming edge or lip 204, similar to the lip 188 of the cartridge 184 of FIGS. 33-36 and having a sloped, non-90° edge, to help move the knife 192 between its non-cutting and cutting positions. Also similar to the other cartridge 184, the slot 196 in the cartridge's proximal region can have a greater depth than in the cartridge's distal region. In this way, when the cutting assembly distally moves through the slot 196 with the knife 192 in the initial position, a distal edge 192*a* of the knife 192 can contact the lip 204. The distal edge 192*a* can include a cutting edge along a partial length thereof, with a bottom portion of the distal edge 192*a* closest to the hinge 194 being more dull than the cutting edge to help prevent the knife 192 from cutting the lip 204 instead of leveraging against the lip 204 and moving over the lip 204 as the hinge 194 bends. Although the knife's pivot point at the hinge 194 is located "below" the lip 204 with the knife 192 in the initial position, the lip 204 can provide adequate leverage for the hinge 194 to flex and bend the knife 192 until corresponding mating edges 190*b* of the knife 192 and the pusher bar's main body 190*a* come into contact and the knife 192 is in its cutting position, as shown in FIGS. 39 and 40. The pusher bar 190 can have a cut-out 190*c* formed therein located between the knife 192 and the main body 190*c*, e.g., above the hinge 194, to accommodate bending of the hinge 194 and movement of the knife 192. Tissue engaged in the tissue gap 202 between the cartridge 198 and the anvil 200 can provide adequate tension to hold the knife 192 in the cutting position during distal translation. The hinge 194 can optionally be configured to permanently deform when the knife 192 bends back against the main body 190*a* to help ensure that the knife 192 stays in the cutting position. Alternative, or in addition, one or both of the mating edges 190*b* can optionally include at least one mating feature, e.g., a snap lock, an adhesive, etc., to hold the mating edges 190*b* together when they move into close enough contact. With the knife 192 rotated in a clockwise direction from the non-cutting position to the cutting position, a bottom edge 190*d* of the pusher bar 190 can move through the longitudinal slot 196 along a lip edge 204*a* forming a bottom surface of the slot 196 in the cartridge's distal, cutting region. Accordingly, the knife 192 in the cutting position in the cartridge's distal region can be configured to cut tissue in the tissue gap 202 using the knife's now distally facing cutting edge 192a.

Similar to that discussed above, if the cutting assembly is pulled proximally after the knife 192 has contacted the lip 204 and the hinge 194 has at least started to bend, the knife 192 in the cutting assembly as illustrated can move back to its non-cutting position from the cutting position. The cartridge 198 in this illustrated embodiment includes at least one return contact 206 formed in or otherwise coupled to a wall of the slot 190 that can have any configuration, as will be appreciated by a person skilled in the art, to engage the knife 192 and push the knife 192 back to its non-cutting position as the knife 192 moves proximally past the return contact 206. The knife 192 can have a corresponding return contact formed thereon or otherwise coupled thereto, e.g., a protrusion, that is configured to engage the slot's return contact 206 to help move the knife 192 from the cutting position to the non-cutting position.

As mentioned above, in some embodiments the cutting element can move proximally through a transector to cut tissue. In such embodiments, the cutting assembly can have an initial, unassembled configuration where the cutting element can be an element independent from a pusher bar configured to move the cutting element through a distal, cutting region of the transector's end effector. Generally, the pusher bar can move distally through the end effector and fasteners can be applied to tissue in the distal, cutting region. Having moved distally far enough through the end effector, the pusher bar can engage the cutting element disposed at a distal end of the end effector and it can be pulled proximally to move the pusher bar with the cutting element attached thereto through the end effector. Pulling the cutting element proximally can keep elements of the cutting assembly linearly aligned and reduce chances of any part of the cutting assembly buckling.

Figure 42:
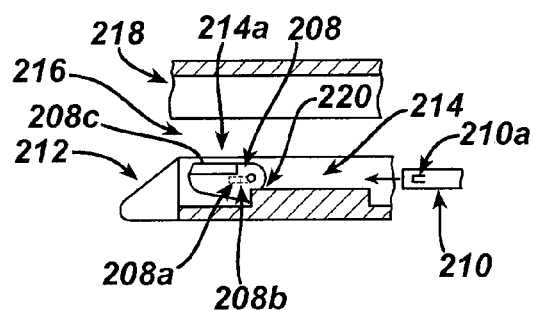
FIG. 42 is a partial cutaway side view of one embodiment of a cutting element disposed in an initial, non-cutting position in a distal end of a pair of jaws having a proximal, cut-free and fastener-free region, and a pusher bar distally moving through the jaws toward the cutting element.
Figure 43:
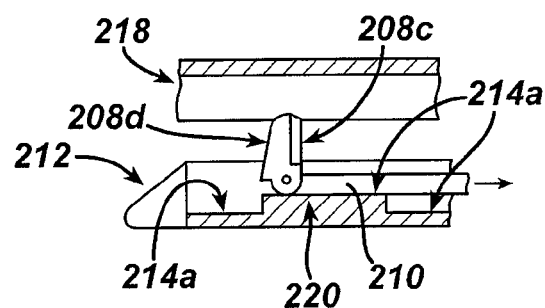
FIG. 43 is a partial cutaway side view of the pusher bar of FIG. 42 coupled to the cutting element and moving proximally through the jaws with the cutting element in a cutting position.
Figure 44:
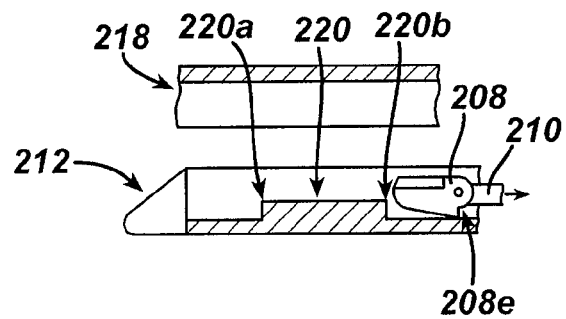
FIG. 44 is a partial cutaway side view of the pusher bar of FIG. 43 coupled to the cutting element and moving proximally through the jaws with the cutting element in the non-cutting position.

One embodiment of a transector having a cutting element that moves proximally is illustrated in FIGS. 42-44. The cutting assembly includes a knife 208 and a pusher bar 210. The knife 208 and the pusher bar 210 can be disconnected from each other in an initial, non-cutting position before at least the knife 208 translates through an end effector including opposed first and second jaws 212, 218. Generally, the pusher bar 210 can move distally through a longitudinal slot 214 in the first jaw 212, as shown in FIG. 42, and it can "grab" the knife 208 when the pusher bar 210 encounters the knife 208 in a distal portion 214a of the slot 214. The pusher bar 210 can be actuated in any way to move the pusher bar 210 distally through the slot 214, as shown in FIG. 42. The pusher bar 210 with the knife 208 attached thereto can be moved proximally through the slot 214 to allow the knife 208 to cut tissue engaged in a distal region of a tissue gap 216 between the first and second jaws 212, 218, as shown in FIG. 43, but not in a proximal, cut-free region of the first and second jaws 212, 218, as shown in FIG. 44. In an exemplary embodiment, one or more fasteners can be applied to tissue in the distal region of the tissue gap 216 before the knife 208 cuts the tissue, e.g., the pusher bar 210 or other fastener driving mechanism ejects one or more fasteners from the end effector, although one or more fasteners can be applied to the tissue as the tissue is cut. Separately cutting tissue and applying fasteners to the tissue can allow more force to be applied to each of tissue cutting and tissue fastening.

The knife 208 and the pusher bar 210 can generally be configured similar to knives and pusher bars discussed above, although the knife 208 and the pusher bar 210 can have corresponding, respective catch mechanisms 208a, 210a formed thereon or otherwise coupled thereto to help the pusher bar 210 "grab" the knife 208. The catch mechanisms 208a, 210a can each have a variety of configurations. The knife's catch mechanism 208a can include a hole formed through the knife 208, while the pusher bar's catch mechanism 210a can include a flex catch configured to engage the hole to attach the knife 208 to the pusher bar 210. The pusher bar's flex catch can be formed in any way, such as by pressing out a tongue in material such as sheet metal that forms the pusher bar 210. The knife 208 can optionally include a flex member 208b extending from the hole as part of the knife's catch mechanism to help the pusher bar's catch mechanism 210a engage the hole. The flex member 208b can be formed similar to the pusher bar's flex catch.

The knife 208 can be pre-positioned in the initial position within the first jaw 212 at the distal portion 214a of the slot 214, while the pusher bar 210 can be pre-positioned 208 in the initial position anywhere proximal to the knife 208, e.g., proximal to a proximal end (not shown) of the slot 214. In the initial position, the knife 208 can be positioned such that a proximal cutting edge 208c of the knife 208 is disposed within the first jaw 212 such that the cutting edge 208c cannot cut tissue engaged in the tissue gap 216 between the jaws 212, 218. Because the knife 208 moves proximally through the end effector to cut tissue, the cutting edge 208c is formed on a proximal side of the knife 208. The knife 208 in the initial position can also be positioned substantially at a distal end of the first jaw 212 with its distal, non-cutting side 208d positioned adjacent a bottom surface 214a of the slot 214 and its proximal cutting edge 208c facing the tissue gap 216. Such positioning can help move the cutting edge 208c into the tissue gap 216 when the pusher bar 210 engages the knife 208 and pulls the knife 208 proximally through the slot 214. A proximal cut-out 208e formed in the knife's distal side 208d can abut a distal-facing edge 220a of a step 220 formed in the slot 214. The step's distal-facing edge 220a can act as a camming edge or lip configured to rotate the knife 208 in a clockwise direction from the initial, non-cutting position to the cutting position when the knife 208 is engaged and pulled proximally by the pusher bar 210. Accordingly, the proximal cut-out 208e and the step's distal-facing edge 220a can have corresponding complementary sizes and shapes. The knife 208 can optionally be removably secured in the initial position in the slot 214 in any way appreciated by a person skilled in the art, such as with a releasable catch mechanism formed on or otherwise coupled to any one or more of the knife 208, the step 220, and the slot 214.

As shown in FIG. 43, when the pusher bar 210 couples to the knife 208 and pulls the knife 208 proximally over the step's distal-facing edge 220a, the knife 208 can be configured to translate along the slot's bottom surface 214, also a top surface of the step 220, with the knife's cutting edge 208c extending into the tissue gap 216 and into a longitudinal slot formed in the second jaw or anvil 218. The knife 208 can thus cut tissue in the distal region of the end effector because the step 220 can be positioned within the slot 214 to correspond with the end effector's distal region. When the knife 208 reaches a proximal edge 220b of the step 220, the knife 208 can rotate substantially back to its initial, non-cutting position, as shown in FIG. 44. In this way, when the knife 208 substantially returns to its initial, non-cutting position proximally beyond the step's proximal edge 220b, the knife 208 can be configured to not cut tissue in the proximal, cut-free region of the end effector. The proximal motion of the pusher bar 210 can move the knife 208 from the cutting position to the non-cutting position such that the knife's distal side 208d moves back into contact with the slot's bottom surface 214a. Optionally, the first and/or second jaw can include a camming edge or lip (not shown) to help move the knife 208 from the cutting position to the non-cutting position. For non-limiting example, the slot 214 in the first jaw 212 can only extend through a tissue-contacting surface of the first jaw 212 in the distal region, similar to the slot 156 in the staple cartridge 154 of FIGS. 23-25, such that a proximal edge of the slot 214 in the tissue-contacting surface can help urge the knife 208 to the non-cutting position.

Figure 45:
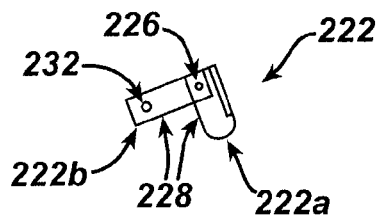
FIG. 45 is a side view of one embodiment of a cutting element including two pivotably connected members.
Figure 46:
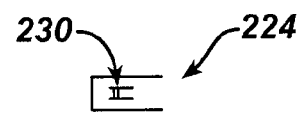
FIG. 46 is a partial side view of one embodiment of a pusher bar configured to couple to the cutting element of FIG. 45.
Figure 47:
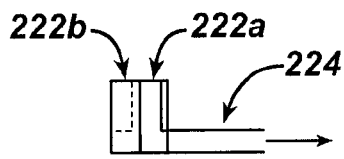
FIG. 47 is a partial side view of the pusher bar of FIG. 46 coupled to the cutting element of FIG. 45, with the cutting element in a cutting position.

A second embodiment of a transector having a cutting element that moves proximally to cut is illustrated in FIGS. 45-47. The cutting assembly includes a knife 222 and a pusher bar 224. The cutting assembly is generally configured as discussed above except that the knife 222 can be configured as a two-part member including distal and proximal members 222a, 222b connected together with a connection mechanism such as a hinge 226. The hinge 226 can include any type of hinge, e.g., a pivoting pin. The knife 222 can be positioned in an initial, non-cutting position in an end effector similar to the knife 208 of FIGS. 42-44 with mating edges 228 of the proximal and distal members 222a, 222b positioned on a slot's bottom surface such that the knife 222 can be in a substantially flat or linear position with longitudinal axes of the proximal and distal members 222a, 222b substantially aligned. In this embodiment, the slot's bottom surface need not include a step as in the embodiment of FIGS. 42-44 because the knife 222 can move into a tissue gap by bending at the hinge 226.

The pusher bar 224 can move distally through the end effector and attach to the knife 222 using a catch mechanism, e.g., with a flex catch 230 configured to engage a hole 232 formed in the knife's distal member 222b. Proximal motion of the pusher bar 224 after the pusher bar 224 has attached to the knife's distal member 222b can apply a force to the distal member 222b, thereby bending the knife 222 at the hinge 226, as shown in FIG. 45, to move the mating edges 228 together and move the knife 222 from the non-cutting position to the cutting position, as shown in FIG. 47. The knife 222 can move back to the non-cutting position for the knife's translation through the end effector's proximal, non-cutting region in any way, as will be appreciated by a person skilled in the art. For non-limiting example, substantially at an intersection between the distal, cutting region and the proximal, non-cutting region of the end effector, the end effector can include at least one return contact formed in the wall of the slot through which the cutting assembly translates in the end effector, similar to that as discussed above regarding FIG. 40. As another non-limiting example, the end effector can include a stop mechanism to stop proximal translation of at least the knife 222 through the end effector, e.g., a camming edge or lip formed at a proximal edge of the slot at a tissue-contacting surface of the end effector.

Figure 48:
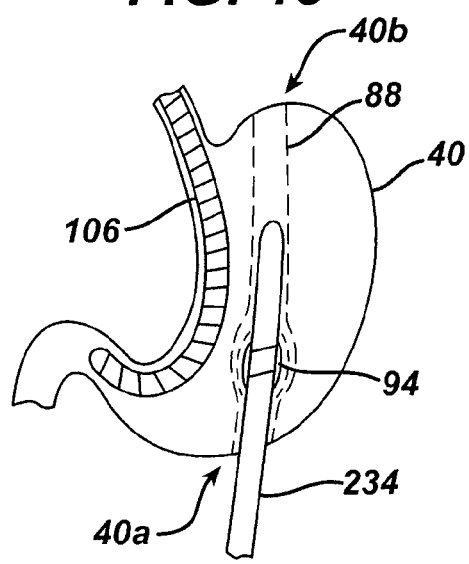
FIG. 48 is a perspective view of one embodiment of a transecting device transecting a portion of a stomach of a patient with a sizer positioned in the stomach.

Because the transector has a distal, cutting region and a proximal, cut-free region, the transector can apply the staples 96 and form the stomach opening 94 at a distance, equal to the longitudinal length $d_p$, from the edge of the stomach 40 at the antrum 40a, as shown in FIG. 15. The remainder of the stomach 40 between the opening 94 and the angle of His 40b can be transected in any way, as will be appreciated by a person skilled in the art, using the same and/or different transector than that used to form the opening 94 and apply the staples 96. In an exemplary embodiment, as shown in FIG. 48, a second transection device 234, such as a linear surgical stapler, can be introduced into the patient 10 through any opening, e.g., through an abdominal access hole, a natural orifice, etc., with or without a single or multiple port access device positioned therein. In an exemplary embodiment, the second transection device 234 can be inserted through the opening 94 in the stomach 40, and it can be used to cut and secure the stomach 40 along a transection "line" in a direction from the opening 94 to the angle of His 40b, using the sizer 106 as a guide until the angle of His 40b is breached. Using a conventional linear stapler instead of a transactor having a proximal cut-free region can allow for fewer strokes of the stapler to complete the transection.

Figure 49:
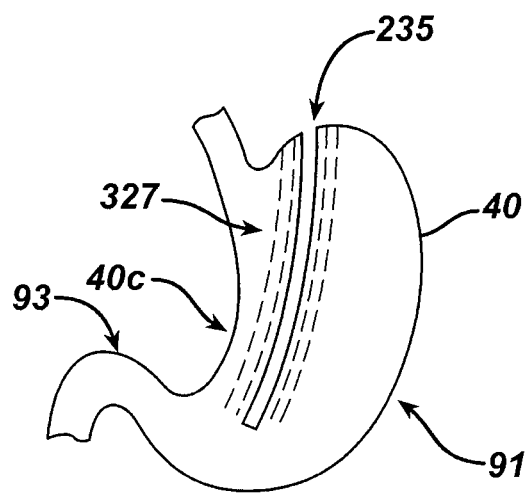
FIG. 49 is a perspective view of one embodiment of a transected stomach.

FIG. 49 shows the stomach 40 having a transection "line" 235 formed therein where a partial length of the stomach 40 has been transected. The transection "line" 325 can generally be an opening in the stomach 40 that is closed or sealed using one or more securing elements, e.g., two rows of staples on either side of the opening. The stomach 40 can thereby be separated by the transection "line" 325 between the lesser curvature 40c and the greater curvature 91 to form a gastric tube or stomach sleeve 327 along the lesser curvature 40c that drains into the antrum 40a. Such a transection can separate the stomach fundus from an area of the stomach 40 substantially near the patient's esophagus and allow the fundus to retain fluid communication with the patient's pylorus 93, and more specifically, with the patient's pyloric valve.

Figure 50:
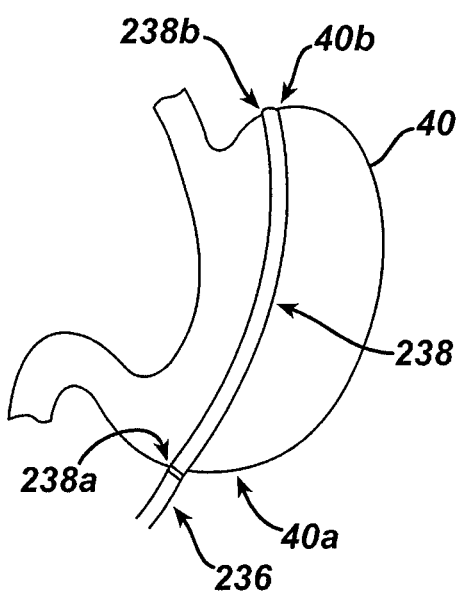
FIG. 50 is a perspective view of one embodiment of a transecting device having an extended length end effector positioned in an initial position to transect a portion of a stomach of a patient.

In an alternate embodiment of a stomach transection, a single transection device can be used to transect a desired length of the stomach 40 in a Magenstrasse and Mill procedure without having to reposition the transector from its initial position engaging the stomach 40. In an exemplary embodiment shown in FIG. 50, an extended length transection device 236 can be positioned relative to the stomach 40 with an end effector 238 of the extended length transection device 236 extending across a length of the stomach 40 between the antrum 40a and the angle of His 40b. A person skilled in the art will also appreciate that an extended-length end effector similar to the extended-length end effector 238 can be used with any transactor described herein. A proximal end 238a of the end effector 238 can be positioned substantially at the antrum 40a with the end effector 238 extending toward the angle of His 40b such that a distal end 238b of the end effector 238b can extend distally beyond the angle of His 40b. The end effector 238 can have any shape, but in an exemplary embodiment it can be arcuate as shown to better approximate a desired transection line that would otherwise be hand-estimated through repeated positioning and actuating of one or more transection devices. The end effector 238 can also have any size and any longitudinal length, e.g., at least about 180 mm. The end effector 238 can have a proximal, cut-free region and a distal, cutting region as discussed above. In this way, the extended length transactor 236 can be used to transect the stomach 40 substantially as shown in FIG. 49 in one or more actuation strokes without having to reposition the end effector 238 of the transactor 236 or reload additional fasteners into the end effector 238, thereby making the surgical procedure faster and safer. Using the extended length transection device 236 to transect the stomach 40 can also reduce the need to retract the patient's liver and/or the need to provide counter traction with a grasper during the transection.

Figure 51:
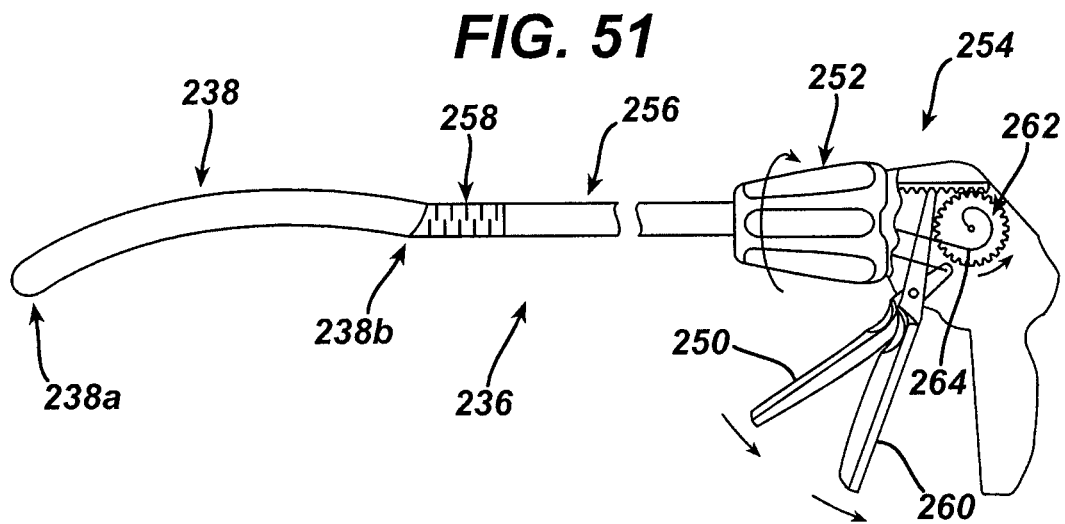
FIG. 51 is a partial side view of the transecting device of FIG. 50.
Figure 52:
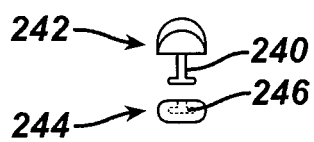
FIG. 52 is a partial distal end view of the end effector of FIG. 51.
Figure 53:
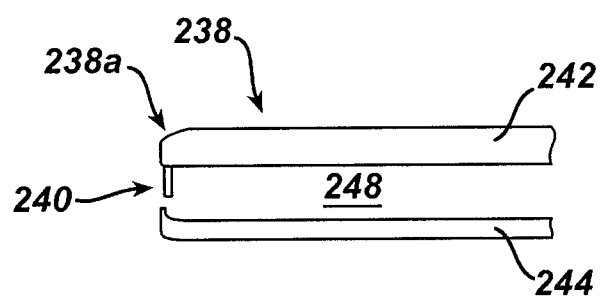
FIG. 53 is a partial side view of the end effector of FIG. 51.

One embodiment of the extended length transector 236 is shown in FIGS. 51-53. Generally, the transector 236 can include a proximal, handle portion 254 having an elongate shaft 256 extending distally therefrom, with the end effector 238 located at a distal end of the elongate shaft 256. One or more staple cartridges each having a plurality of staples loaded therein can be loaded into the end effector 238, although any type of fasteners can be used as mentioned above. If multiple staple cartridges are loaded into the end effector 238, the staple cartridges can have the same or different longitudinal lengths and the same or different size staples from any other cartridge loaded in the end effector 238. In this way, variable thicknesses of the stomach 40 can be accommodated by the transector 236. In some embodiments, the fasteners can be disposed in an end effector of a transector without a cartridge such that the transector is a single use device.

Figure 54:
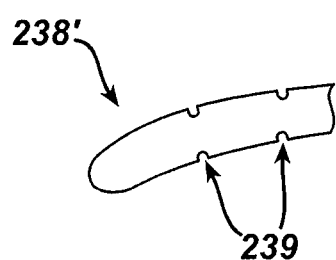
FIG. 54 is a perspective view of one embodiment of an end effector of a transecting device having a plurality of notches formed therein.

The jaws 242, 244 can be drawn together with tissue engaged in at least a portion of a tissue gap 248 between the opposed jaws 242, 244, e.g., by actuating a first, clamping handle 250 in the handle portion 254. However, before clamping tissue to be transected between opposed, first and second jaws 242, 244 of the end effector 238, the end effector's position within a patient's body can be adjusted to desirably position the end effector 238 adjacent tissue to be cut and fastened. The transector 236 can include a rotation knob 252 configured to rotate the end effector 238 and optionally the elongate shaft 256 relative to the handle portion 254 to help position the end effector 238 in a desired position with a body of a patient. The transector 236 can also or instead include a flex region 258 located at a proximal end 238b of the end effector 238 that can be configured to bend the end effector 238 relative to the elongate shaft 256. While the flex region 258 can be flexed by actuating a control mechanism at the transector's handle portion 254, a person skilled in the art will appreciate that the flex region 258 can be passively flexed by positioning the end effector 238 against a surface to cause flexion. A person skilled in the art will also appreciate that the elongate shaft 256 and/or the end effector 238 can include one or more flex regions or flexible joints, and that each can be configured in any way, as discussed above. As shown in an alternate embodiment of a transector end effector 238' in FIG. 54, the end effector 238' can include a flexible joint in the form of a plurality of slots or notches 239 formed in the end effector 238' such that the end effector 238' has a reduced cross-section where each of the notches 239 are formed. An elongate shaft from which the end effector 238' extends can alternatively, or in addition, include similar slots or notches.

To accommodate the proximal, cut-free region in the end effector 238, the transector 236 can be configured with a cutting element and a staple driver disposed in an initial, non-cutting position at a distal end 238a of the end effector 236. As shown in FIG. 53, the cutting element and the staple driver can be in the form of an I-beam 240 configured to cut tissue using a cutting edge on a proximal side of the I-beam 240 and to drive staples, although, as will be appreciated by a person skilled in the art, the cutting element and the staple driver can be separate elements. The I-beam 240 cab be disposed in one of the first and second jaws 242, 244, and the other one of the jaws 242, 244 can have an opening 246 at a distal end thereof to receive the I-beam 240 when the jaws 242, 244 are moved from an open to a closed position. The stomach's angle of His can provide clearance space in the patient that can provide adequate space for the I-beam 240 at the distal end 238a of the end effector 236 to engage the opening 246. A person skilled in the art will appreciate that the end effector 238 can be augmented with buttress material to provide it with additional structural support.

The I-beam 240 can be configured to translate along a partial longitudinal length of the end effector 238 in any way appreciated by a person skilled in the art, e.g., by actuating a driving handle 260 in the handle portion 254. Actuation of the driving handle 260 can proximally pull the I-beam 240 along the end effector 238 to fasten and/or cut tissue in the tissue gap 248, although in some embodiments the transector 236 can be distally driven rather than proximally driven to cut tissue. Movement of the I-beam 240 through the end effector 238 can also help reduce flex of the jaws 242, 244 if a large amount of tissue is engaged between the jaws 242, 244. Actuation of the driving handle 260 can proximally pull the I-beam 240 in any way appreciated by a person skilled in the art, such as by winding a wire 264 connected at its respective terminal ends to a reel 262 in the handle portion 254 and to the I-beam 240 such that winding of the wire 264 around the reel 262 proximally moves the I-beam 240 through the end effector 238.

The I-beam 240 can be configured to cut tissue engaged in the distal, cutting region of the end effector 238 without cutting tissue engaged in the proximal, non-cutting region of the end effector 238 in a variety of ways. For non-limiting example, complete actuation of the driving handle 260 can be configured to move the I-beam 240 only a partial distance along the length of the end effector 238. As another non-limiting example, the end effector 238 can include a stop mechanism located substantially at an intersection of the distal and proximal regions and configured to stop proximal movement of the I-beam 240 once the I-beam contacts the stop mechanism. One embodiment of a stop mechanism includes a proximal edge of the channel 246 through which the I-beam 240 translates in one of the jaws 242, 246 and/or in a channel in which the I-beam 240 moves in the jaw to which it is attached.

However performed, the transection can be visualized using at least one scoping device inserted through any opening, as discussed herein. For non-limiting example only, the surgeon can visualize above and/or underneath the stomach 40 to determine if a desired path of transection is clear or readily cleared of tissue and/or other debris. The surgeon can place one or more draining devices in the stomach fundus following the transection, e.g., along a greater curvature of the stomach sleeve formed by the transection. If used, the sizer 106 can be removed from the stomach 40 at any time during the surgical procedure, but in an exemplary embodiment it is removed from the patient 10 by retracting it through the patient's mouth 108 after the stomach 40 has been transected and inspected via scoping device visualization for any uncorrected and potentially dangerous irregularities, e.g., improperly bent staples, improperly placed staples, untied sutures, etc.

The surgeon can optionally secure the transected stomach, e.g., along the stapled or otherwise secured cut edge of the fundus, using any one or more supplemental securing elements in any combination to help better secure the transection and/or reduce bleeding. The supplemental securing elements are preferably biocompatible and can optionally be bioabsorbable such that the supplemental securing elements can dissolve in the patient 10 over time as the transection heals. Non-limiting embodiments of a surgical stapler than can apply staples with bioabsorbable pledgets can be found in previously filed U.S. patent application Ser. No. 11/541,374 of Hess et al. filed on Sep. 29, 2006 and entitled "Surgical Staples Having Dissolvable, Bioabsorbable Or Biofragmentable Portions And Stapling Instruments For Deploying The Same," which is hereby incorporated by reference in its entirety.

At the conclusion of a gastroplasty, any access holes formed in a patient can be closed in any way and in any order as will be appreciated by a person skilled in the art, such as by suturing the openings.

The patient 10 can optionally be provided with a drug and/or device that suppresses appetite that can work in conjunction with the stomach sleeve to help the patient 10 lose weight. Such a drug or device can be provided to the patient 10 at the end of the gastroplasty and/or in a subsequent surgical procedure. A non-limiting embodiment of an implantable appetite suppressant device is available from Duocore, Inc. of Ramat-Hasharon, Israel.

A gastroplasty procedure described herein can optionally be combined with one or more other surgical procedures. For non-limiting example, the gastroplasty can be combined with a transoral minimally invasive surgical procedure, non-limiting examples of which, e.g., creating a gastroenteroanastomosis or enteroenteroanastomosis, can be found in U.S. Patent Application No. 2006/0271075 filed May 18, 2006 and entitled "Double Loop Gastric Bypass Procedure," which is hereby incorporated by reference in its entirety. As another non-limiting example, the gastroplasty can be performed as a first stage of a two stage surgical procedure where a second stage, e.g., a duodenal switch, a Roux-en-Y procedure, etc., can be performed immediately after the gastroplasty or in a subsequent surgical procedure.

A person skilled in the art will appreciate that the present invention has application in conventional endoscopic and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   first and second jaws configured to be movable relative to one another and configured to engage tissue therebetween, the first jaw having a first tissue-engaging surface and the second jaw having a second tissue-engaging surface, the first and second tissue-engaging surfaces facing each other substantially along entire length thereof, and least one of the first and second jaws including a surface feature extending from an interior surface thereof; and
   a knife configured to translate between proximal and distal ends of the first and second jaws, the knife being movable between a proximal region of the first and second tissue-engaging surfaces of the first and second jaws and a distal region of the first and second tissue-engaging surfaces of the first and second jaws, tissue not being cut throughout the proximal region and tissue being cut in the distal region, the knife being in a first position in the proximal region and in a second position in the distal region, and the knife including a complementary feature formed therein that is complementary to the surface feature and is configured to engage the surface feature to move the knife between the first and second positions, wherein the proximal region comprises at least about 20% of a total length extending between the proximal and distal ends of the first and second jaws.

2. The device of claim 1, wherein the knife is configured to pivot between the first and second positions as the knife translates through the first and second jaws.

3. The device of claim 2, wherein the complementary feature includes a cut-out formed in the knife that is configured to allow the knife to pivot between the first and second positions.

4. The device of claim 1, wherein the knife is configured to translate in a distal to proximal direction through the first and second jaws to cut tissue.

5. The device of claim 1, wherein the knife is configured to translate in a proximal to distal direction through the first and second jaws to cut tissue.

6. The device of claim 1, wherein the second position is rotated about 90° from the first position.

7. The device of claim 1, wherein, when the complementary feature includes a cut-out formed in the knife.

8. The device of claim 7, wherein, when the knife is in the second position, the cut-out is formed in a distal-facing side of the knife cutting element.

9. The device of claim 7, wherein, when the knife is in the second position, the cut-out is formed in a proximal-facing side of the knife.

10. The device of claim 1, wherein the proximal region comprises up to 70% of the total length extending between the proximal and distal ends of the end effector.

11. A surgical device, comprising:
    an elongate shaft;
    an end effector coupled to a distal end of the elongate shaft, the end effector configured to engage tissue, and the end effector having a longitudinal slot formed in a distal region thereof but not in a proximal region thereof such that the longitudinal slot extends along a partial longitudinal length of the end effector; and
    a cutting blade configured to translate between proximal and distal ends of the end effector and throughout entireties of the proximal and distal regions, the cutting blade having a first position in the proximal region of the end effector in which tissue is not cut and having a second position in the distal region of the end effector in which tissue is cut, the cutting blade being movable between the first and second positions, and the cutting blade extending through the longitudinal slot in the distal region.

12. The device of claim 11, wherein the cutting blade is configured to translate in a distal to proximal direction along the end effector to cut tissue.

13. The device of claim 11, wherein the cutting blade is configured to rotate between the first and second positions.

14. The device of claim 11, further comprising a cam element configured to move the cutting blade from one of the first and second positions to another of the first and second positions during translation of the cutting blade along the end effector.

15. The device of claim 11, wherein the proximal region comprises at least about 20% of a total length extending between the proximal and distal ends of the end effector.

16. The device of claim 11, wherein the proximal region has a longitudinal length at least as long as a longitudinal length of the distal region.

17. The device of claim 11, wherein the proximal region has a length in a range of about 20% to 70% of a total length extending between the proximal and distal ends of the end effector.

* * * * *